United States Patent
Tsutsui et al.

(10) Patent No.: US 10,349,907 B2
(45) Date of Patent: Jul. 16, 2019

(54) RADIOGRAPHIC IMAGING DEVICE

(71) Applicant: Shimadzu Corporation, Kyoto-shi (JP)

(72) Inventors: Kazuhiko Tsutsui, Kyoto (JP); Shouta Satou, Kyoto (JP); Keiichi Gotoh, Kyoto (JP); Takanori Yoshida, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 174 days.

(21) Appl. No.: 15/328,049

(22) PCT Filed: Jul. 17, 2015

(86) PCT No.: PCT/JP2015/070615
§ 371 (c)(1),
(2) Date: Jan. 22, 2017

(87) PCT Pub. No.: WO2016/013531
PCT Pub. Date: Jan. 28, 2016

(65) Prior Publication Data
US 2017/0209109 A1 Jul. 27, 2017

(30) Foreign Application Priority Data
Jul. 23, 2014 (JP) .................. 2014-149804

(51) Int. Cl.
*A61B 6/00* (2006.01)
*A61B 6/12* (2006.01)

(52) U.S. Cl.
CPC ............... *A61B 6/461* (2013.01); *A61B 6/12* (2013.01); *A61B 6/467* (2013.01); *A61B 6/5241* (2013.01)

(58) Field of Classification Search
CPC .......... A61B 6/00; A61B 6/461; A61B 6/467; A61B 6/5241; A61B 6/503; A61B 6/504;
(Continued)

(56) References Cited

U.S. PATENT DOCUMENTS 9,082,158 B2 * 7/2015 Chen ...................... G06T 5/003
2008/0317195 A1 12/2008 Kobayashi et al.

FOREIGN PATENT DOCUMENTS

JP 2009-022733 2/2009

OTHER PUBLICATIONS

International Search Report dated Oct. 20, 2015, PCT/JP2015/070615.

* cited by examiner

*Primary Examiner* — Jurie Yun
(74) *Attorney, Agent, or Firm* — Muir Patent Law, PLLC

(57) ABSTRACT

The disclosure provides a radiographic imaging device that improves visibility by preventing a phenomenon in which a stent image is inverted in an enlarged displayed video of a stent image that appears in a live image. Specifically, the present disclosure is provided with a trimming unit that performs editing such that, from among two stent markers indicating the position of a stent image that appears in a superimposed frame generated by superimposing source frames that serve as the source of a live image, a specific stent marker is constantly oriented in the same direction on the frame. As a result of using the trimming unit to edit superimposed frames that are continuously generated, a problem seen in the prior art wherein an object to be displayed within video playback is inverted does not occur.

22 Claims, 19 Drawing Sheets

(58) Field of Classification Search
CPC ......... A61B 6/486; A61B 6/0492; A61B 6/12; G01R 33/56; G01R 33/563; G01R 33/5635; G06T 2207/10116; G06T 2207/10124
USPC .................. 378/62, 98.2, 162; 382/130, 132
See application file for complete search history.

| Purpose of imaging | Reference point | Tube current | Tube voltage | Pulse width | Pulse interval |
|---|---|---|---|---|---|
| Right coronary artery imaging | Right upper end | 100 mA | 10 kV | 100 msec | 100 msec |
| Left coronary artery imaging | Left upper end | 100 mA | 8 kV | 100 msec | 100 msec |

Fig. 16

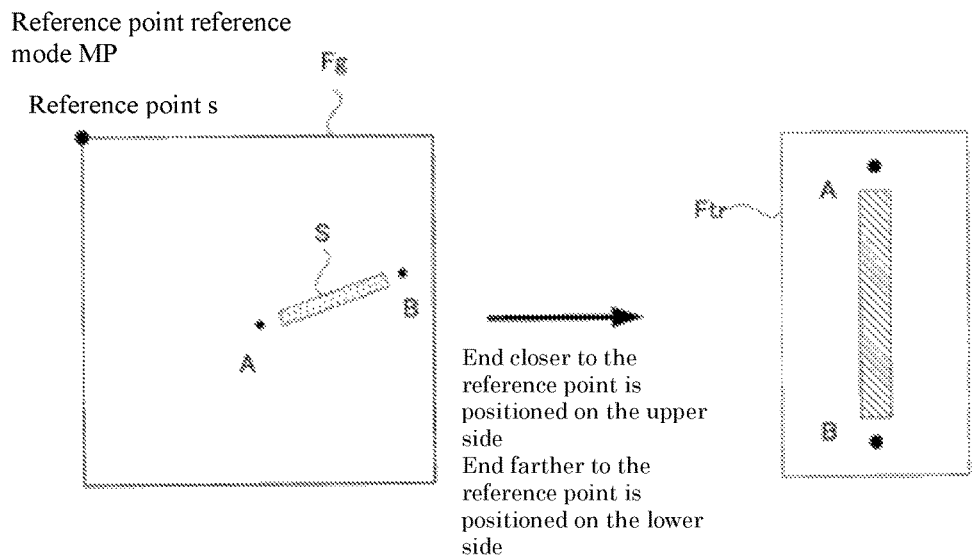

Reference point reference mode MP

Reference point s

End closer to the reference point is positioned on the upper side
End farther to the reference point is positioned on the lower side

Fig. 17

Left and right reference mode MH
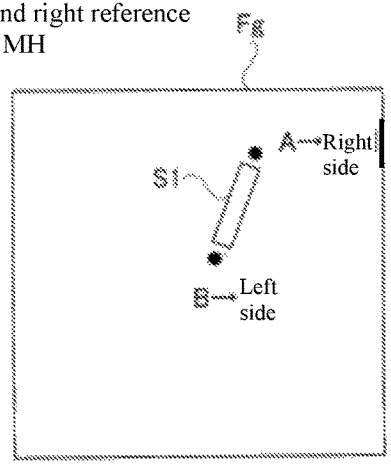
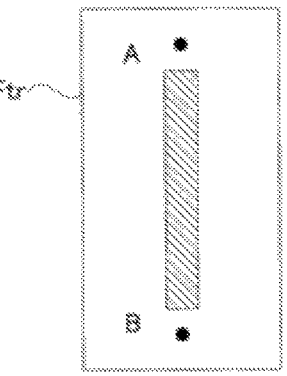
Right side end is positioned on the upper side
Left side end is positioned on the lower side
Fig. 22
Left and right reference mode MH
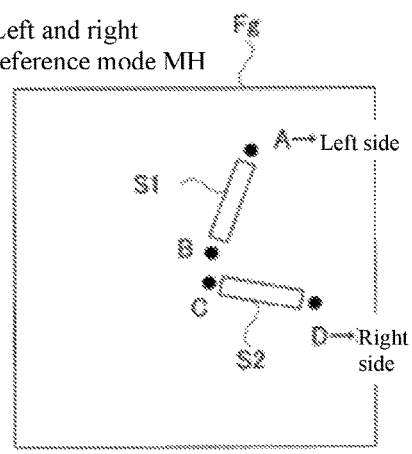
Inverted
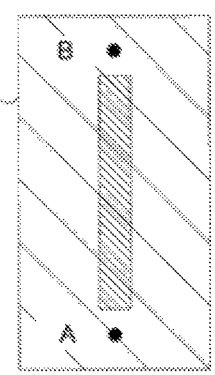
Right side end is positioned on the upper side
Left side end is positioned on the lower side
Fig. 23

RADIOGRAPHIC IMAGING DEVICE

TECHNICAL FIELD

The present disclosure relates to a radiographic imaging device that acquires an image by irradiating radiation to a subject, and especially to a surgical radiographic imaging device for introducing a stent.

TECHNICAL BACKGROUND

In a coronary intervention (PCI) which is a treatment to be carried out for myocardial infraction or angina pectoris, a treatment is carried out such that a catheter equipped with a guide wire therein is inserted from a base of a thigh, etc., into a blood vessel so that the catheter is reached the coronary artery of the heart via the blood vessel. As the device for the coronary intervention treatment, a stent is used. This stent is a medical device made of metal, such as a stainless-steel, and is used to improve treatment effects of a catheter treatment by staying at a stenosis part of a coronary artery expanded using a balloon and holding the blood vessel from the inner cavity. In this case, for example, in cases where a slight gap is generated between a previously arranged stent and a newly arranged stent, there is a possibility that the gap causes angiostenosis. Therefore, an accurate recognition of the stent position may be an important element in a coronary intervention treatment (see, for example, Patent Document 1).

According to a conventional configuration, radiation photographic images (e.g., frames) that form live images are superimposed with reference to a stent marker, so that an image in which the stent and vicinity thereof has become clear is generated. In this image, the stent of the subject and vicinity thereof appear clearer than each frame.

The generation method of this composite image will be specifically explained. Each frame configuring a live image is subjected to an image analysis, so that the position of the stent marker in each frame is specified. Then, each frame is subjected to movement processing and rotation processing so that stent markers that appear in each frame come to the same position. Frames in which the position and the inclination are adjusted with reference to the stent markers are superimposed to thereby generate a superimposed frame. In this superimposed frame, the stent which became clearer by being superimposed on each frame appears. Since this superimposed frame is enlarged for the purpose of obtaining better visibility, it may be required to perform a trimming processing on the superimposed frame before displaying the superimposed frame on a monitor. For example, a part of the superimposed frame in which the stent appear is trimmed, so that a trimming frame is generated. This trimming frame includes an image in which the stent appeared small in the superimposed frame was taken out of the superimposed frame and displayed in an enlarged manner.

It is configured such that this trimming frame is sequentially updated during imaging of the live image and that the monitor displaying the trimming frame always displays the updated trimming frame. Therefore, the monitor displays this trimming frame as a frame configuring a moving image. This moving image of the trimming frame is a moving image chasing the clearly enlarged stent appearing small in the live image with time.

PRIOR ART DOCUMENT

Patent Document

Patent Document 1: Japanese Unexamined Patent Application No. 2009-022733

SUMMARY

Problems to be Solved by the Present Disclosure

However, a conventional radiographic imaging device configured as mentioned above has following problems. For example, according to a conventional device, the display (orientation) of the moving image showing a stent and periphery thereof is unstable, which confuses an operator.

The stent appears in the live image while changing its appearing position and orientation. In most cases, a stent merely moves in parallel in the live image in accordance with the heartbeat of a subject, and therefore when the position of the stent may be recognized, the image processing of superimposing the images of the stent appearing in each frame is not so difficult.

However, even if the orientation of the stent is accurately grasped, it becomes difficult to superimpose the frames. This problem will be described below. FIG. 26 illustrates the procedure of generating a trimming frame based on three frames F1, F2, and F3 configuring a live image. According to a conventional device, focusing on both ends (e.g., opposite ends) of a stent that appears in each frame F1, F2, and F3, the movement and rotation operations of the frame are executed. Among both ends of the stent, the artery end side is denoted as an end A, while the vein end side is denoted as an end B. Therefore, the blood in the blood vessel in which a stent is provided flows from the end A toward the end B.

In each frame F1, F2, and F3, the stent appears while changing its position. A conventional device generates a superimposed frame with the position and the inclination of each frame F1, F2, and F3 so that the upper and lower ends of the stent that appear in the frame are overlapped, respectively. In the case of FIG. 26, the upper end of the stent that appears in each frame F1, F2, and F3 is positioned at the artery side end A, and therefore the superimposed frame is generated with the ends A of stents in frames overlapped. Further, the lower end of the stent that appears in each frame F1, F2, and F3 is positioned at the vein side end B, and therefore the superimposed frame is generated with the ends B of stents in frames overlapped. In the stent that appears in this superimposed frame, in the same manner as in each frame, the upper side of the stent is the end A and the lower side thereof is the end B. In order to simplify the explanation, in FIG. 26, it is assumed that no rotation of the frame is required to generate the superimposed frame.

The superimposed frame generated as mentioned above is subjected to trimming processing. The trimmed frame obtained by the trimming processing is, for example, a vertically elongated image in which the stent extending in the vertical direction appears at the center. However, there may be a problem in determining which end of the stent should be positioned on the upper side of the trimmed frame. According to a conventional device, the orientation of the stent in the trimming frame is determined so that, for example, the upper end of the stent that appears in the superimposed frame is positioned on the upper side of the trimming frame. Referring again to FIG. 26, the stent that appears in this superimposed frame, the upper side thereof is set as the end A. Therefore, the orientation of the trimming frame is determined such that the end A is set as the upper side and the end B is set as the lower side. The stent appears in the trimming frame so that the blood flows in the direction from the upper side toward the lower side as shown by the arrow in FIG. 26.

Here, it is assumed that an operator adjusts the imaging orientation of the live image. It is also assumed that the subject that appears in the live image is rotated by the adjustment. For example, as shown in FIG. 27, a change in position of the stent may happen such that the end A of the stent which was positioned on the upper side of the live image before the rotation moves toward the lower side and the end B of the stent of the live image before the rotation moves toward the upper side.

Hereinafter, it is considered what trimming frame is generated based on each frame F4, F5, and F6 as shown in FIG. 28 generated after the change of appearance of the stent as shown in FIG. 27. A conventional device generates a superimposed frame with the position and the inclination of each frame F4, F5, and F6 aligned so that the upper and lower ends of the stents that appear in the frame are overlapped, respectively. In the case shown in FIG. 28, the upper end of the stent that appears in each frame F4, F5, and F6 is the vein side end B, and therefore the superimposed frame is generated with the ends B of stents on frames overlapped. Further, the lower end of the stent that appears in each frame F4, F5, and F6 is the artery side end A, and therefore the superimposed frame is generated with the ends A of stents in frames overlapped. In the stent that appears in this superimposed frame, in the same manner as in each frame, the upper side of the stent is the end B and the lower side thereof is the end A.

The superimposed frame generated as mentioned above is subjected to trimming processing. The trimmed frame obtained by the trimming processing is an elongated image as mentioned above. According to a conventional device, the orientation of the stent in the trimming frame is determined such that, for example, the upper end of the stent that appears in the superimposed frame is positioned on the upper side of the trimming frame. The stent that appears in the superimposed frame shown in FIG. 28, since the upper end is the end B, the orientation of the stent in the trimming frame is determined such that the end B is the upper side and the end A is the lower side. The stent appears in the trimming frame so that the blood flows in the direction from the lower side toward the upper side as shown by the arrow in FIG. 28.

Here, it should be noted that the trimming frame shown in FIG. 26 and the trimming frame shown in FIG. 28 are in a relation that when one of the trimming frames is rotated by 180 degrees, the one of the trimming frames becomes the other trimming frames. The trimming frame shown in FIG. 26 and the trimming frame shown in FIG. 28 look the same at a glance, but the upper end of the stent that appears in the trimming frame is not the same in FIG. 26 and FIG. 28. The upper end in FIG. 26 is the end A, on the other hand, the upper end in FIG. 28 is the end B. For example, in some cases, the orientation of the stent may be inverted as shown in FIG. 29 when each trimming frame is being displayed as a frame of a moving image.

Such a configuration which allows the inversion of the stent image in the trimming frame during the display of the moving image makes it difficult for the operator to to do the work. When the operator looks at the upper side of the moving image to perform the work on the vein side of the stent, the orientation of the stent that appears in the moving image inverses at a certain time. This forces the operator to perform the work by looking at the lower side of the moving image. When the inversion of the moving image happens, the right and left relation reverses, which further confuses the operator.

Such inversion of the moving image (trimming image) of the trimming frame may not always occur only when an operator adjusts the imaging orientation of a live image. As shown in FIG. 30, in cases where the stent appears sideways in the live image, an inversion of the trimming image may sometimes occur. The principal of occurrence of the inversion will be explained. The stent appears in the live image while slightly changing its inclination angle. For example, as shown in FIG. 30, the right end of the stent in the moving image is positioned on the upper side or on the lower side. When such up-and-down relation of the stent in the live image is unstable, the display of the moving image in the trimming frame also becomes unstable, which sometimes causes inversion of the moving image.

For example, in a conventional device, when generating a trimming frame, editing, such as rotational editing of the superimposed frame, is required. In cases where the stent that appears in the superimposed frame is oriented right side and in cases where the stent appears in the superimposed frame so as to extend from the left lower side toward the right upper side, the superimposed frame is rotated clockwise. On the other side, in cases where the stent appears in the superimposed frame so as to extend from the left upper side toward the right lower side, the superimposed frame is rotated counterclockwise. Therefore, depending on the inclination orientation of the stent, the end of the stent in the trimming frame is positioned on the upstream side or downstream side of the blood vessel. For example, in the moving image in the trimming frame, the display of the stent that appears in the trimming frame is inverted in the middle of reproduction, resulting in poor visibility.

Further, depending on the shape of the stent that appears in the superimposed frame, it may not be determined which end of the stent is positioned on the upstream side or downstream side of the blood vessel. This is because the stent is left-right symmetry in most cases.

The present disclosure was made in view of the aforementioned circumstances, and its purpose is to provide a radiographic imaging device improved in visibility by preventing a phenomenon in which a stent image reverses in a moving image in which a stent image that appears in a live image is enlarged.

Means for Solving the Problems

The present disclosure has the following configuration to solve the aforementioned problems. For example, a radiographic imaging device includes:

a radiation source that irradiates radiation toward a subject;

detection means that detects the radiation passed through the subject;

source frame generation means that generates a source frame based on a detection signal output by the detection means;

alignment processing means that recognizes a plurality of feature points indicating a position of an object that appears in the source frame continuously generated and aligns the source frames so that corresponding feature points overlap with each other;

superimposed frame generation means that repeatedly generates a superimposed frame in which images of the object overlap with each other by superimposing the aligned source frames; and editing means that repeatedly performs editing on each of the superimposed frames so that a particular one of the feature points that appear in the successively generated superimposed frame orients in the same direction on the frame.

[Functions and Effects] According to the present disclosure, a radiographic imaging device may be provided in which in a moving image displaying an enlarged stent image S that appears in a live image, the visibility is improved by preventing the phenomenon of inverting the stent image S. For example, according to exemplary embodiments, the radiographic imaging device is equipped with the editing means that performs editing that a specific one of a plurality of features, which shows a position of a stent image that appears in a superimposed frame Fg generated by superimposing source frames F which are sources of the live image VL, is made to be always oriented in the same direction on the frame. By editing a superimposed frame Fg continuously generated by the editing means, an object appears in the edited frame in the same orientation. Therefore, a phenomenon that an object to be display is inverted during the video playback as seen in the past may not occur.

The disclosed invention, according to exemplary embodiments, can prevent an inversion of an object to be displayed, and therefore is suitable for blood vessel imaging. In the blood vessel imaging, a blood vessel appears in a superimposed frame. When the display of the superimposed frame is inverted like in a conventional configuration, the blood vessel that appears in the superimposed frame is also inverted, the downstream side and the upstream side of the blood vessel that appears in the superimposed frame is inverted. In such a situation, it becomes undistinguishable which side of the superimposed frame is the heart side, making it difficult to perform an operation. According to the present disclosure, sine the display of the superimposed frame is not inverted, the downstream side and the upstream side of the blood vessel that appears in the superimposed frame is not inverted, which results in an easy operation.

Further, in the aforementioned radiographic imaging device, it is more desirable that the editing means determines one of features appearing in the superimposed frame that becomes a reference of the editing based on a positional relationship of the feature point or an instruction of an operator.

[Functions and Effects] The aforementioned configuration shows a specific configuration of the disclosed invention according to exemplary embodiments. For example, by determining one of features appearing in the superimposed frame that becomes a reference of the editing based on a positional relationship of stent markers or an instruction of an operator, the editing means may be operated more assuredly.

Further, in the radiographic imaging device, it is more preferable that the editing means operates so as to repeatedly generate a trimming frame in which the object largely appears every superimposed frame by subjecting trimming processing to each of the superimposed frames so as to remain a rectangular region including the object.

[Functions and Effects] The aforementioned configuration shows a specific configuration of disclosed invention according to exemplary embodiments. When the editing means operates so as to generate a trimming frame, the peripheral portion which is unnecessary when an object is visually observed is trimmed, and therefore the visibility of the object is further improved.

In the radiographic imaging device, it is more desirable to further include input means that allows an operator's input of selecting an upper and lower reference mode that determines an orientation of the editing by determining that an upper end and a lower end of an object that appears in the superimposed frame appear in any one of an upper side, a lower side, a left side, or a right side of the frame.

[Functions and Effects] The aforementioned configuration shows a specific configuration of the disclosed invention according to exemplary embodiments. According to the aforementioned configuration, the form of deciding the orientation of editing the superimposed frame is configured to select the upper and lower reference mode focusing on the upper and lower positional relationship of an object. In a live image in which the left-right relationship of the object frequently inverts, the vertical relationship of the object is stable. In this case, when the upper and lower reference mode is selected, the object in the frame is not inverted.

Further, in the aforementioned radiographic imaging device, when the upper and the lower reference mode is selected, it may be configured such that the editing means determines the orientation of the editing so that the upper end of the object appeared in the superimposed frame is positioned on the upper end of the trimming frame and the lower end of the object appeared in the superimposed frame is positioned on the lower end of the trimming frame.

Further, in the aforementioned radiographic imaging device, it is more desirable to further include input means that allows an operator's input of selecting a left and right reference mode that determines an orientation of the editing by determining that a right end and a left end of an object that appears in the superimposed frame appear in which one of an upper side, a lower side, a left side, or a right side of the frame.

[Functions and Effects] The aforementioned configuration shows a specific configuration of the disclosed invention according to exemplary embodiments. According to the aforementioned configuration, the form of deciding the orientation of editing the superimposed frame is configured to select the left and right reference mode focusing on the left-right relationship of an object. In a live image in which the upper-lower relationship of the object frequently inverts, the left-right relationship of the object is stable. In this case, when the left and right reference mode is selected, the object in the frame is not inverted.

Further, in the radiographic imaging device, it may be configured such that, when the left and right reference mode is selected, the editing means determines the orientation of the editing so that the right end of the object appeared in the superimposed frame is positioned on the upper end of the trimming frame and the left end of the object appeared in the superimposed frame is positioned on the lower end of the trimming frame.

Further, in the radiographic imaging device, it may be configured such that, when the left and right reference mode is selected, the editing means determines the orientation of the editing so that the right end of the object appeared in the superimposed frame is positioned on the right end of the trimming frame and the left end of the object appeared in the superimposed frame is positioned on the left end of the trimming frame.

[Functions and Effects] The aforementioned configuration shows a specific configuration of the disclosed invention according to exemplary embodiments. For example, the orientation of the trimming frame Ftr in the upper and lower reference mode MV of the present disclosure may be set so that the upper end and the lower end of an object appear on the upper side and the lower side of the trimming frame Ftr, respectively. Further, the orientation of the trimming frame Ftr in the left and right reference mode MV of the present disclosure may be set so that the right end and the left end of an object appear on the right side and the left side of the trimming frame, respectively. In the same manner, the orientation of the trimming frame in the left and right reference mode of the present disclosure may be set so that the right end and the left end of an object appear on the upper side and the lower side of the trimming frame, respectively. Which orientation of the trimming frame should be determined depends on the layout on the screen when the trimming frame is displayed. An operator can select the orientation of the frame which is the most visible trimming frame.

Further, in the aforementioned radiographic imaging device, it is more preferable to further include input means that allows an operator's input of selecting a feature point specification mode that determines an orientation of the editing by determining that one of a plurality of features specified by an operator that appears in the superimposed frame appear which one of an upper side, a lower side, a left side, or a right side of the frame.

[Functions and Effects] The aforementioned configuration shows a specific configuration of the present disclosure. According to the aforementioned configuration, the form of deciding the orientation of editing the superimposed frame is configured to select the feature specification mode focusing on the featured specified by an operator. When the feature specification mode is selected, the object in the frame is not inverted.

Further, in the radiographic imaging device, it is more preferable to further include input means that allows an operator's input of selecting a reference point reference mode that determines an orientation of the editing by determining that a feature closer to a reference point and a feature farther to the reference point among a plurality of feature points that appears in the superimposed frame appears in any one of an upper side, a lower side, a left side, or a right side of the frame.

[Functions and Effects] The aforementioned configuration shows a specific configuration of the disclosed invention according to exemplary embodiments. According to the aforementioned configuration, the form of deciding the orientation of editing the superimposed frame is configured to select the reference point reference mode focusing on the distance between the reference ping on the superimposed frame and the feature point. According to this mode, even if the object rotates, the object in the frame is not inverted.

Further, in the radiographic imaging device, it is more desirable to further include input means that allows an operator's input of selecting a reference point reference mode that determines an orientation of the editing by determining that a feature belonging to a region specified on the superimposed frame among among a plurality of feature points that appears in the superimposed frame appears in any one of an upper side, a lower side, a left side, or a right side of the frame.

[Functions and Effects] The aforementioned configuration shows a specific configuration of exemplary embodiments of the present disclosure. According to the aforementioned configuration, the form of deciding the orientation of editing the superimposed frame is configured to select the region reference mode focusing on the position of the feature point in the superimposed frame. According to this mode, even if a plurality of objects appear in the superimposed frame, the object in the frame is not inverted.

Further, in the aforementioned radiographic imaging device, it is more preferable that the object be a stent.

[Functions and Effects] The aforementioned configuration shows a specific configuration of exemplary embodiments of the present disclosure. When the object is a stent, the edited frame according to the present disclosure becomes a frame in which a stent that partially appears in the source. Such a frame effectively assists the operator's operation. Therefore, according to the aforementioned configuration, it becomes possible to provide an improved radiographic imaging device to make it easier for an operation to operate.

Further, in the aforementioned radiographic imaging device, it is more desirable to further include display means that displays a live image which is a moving image configured by the source frame and an edited frame side by side.

[Functions and Effects] The aforementioned configuration shows a specific configuration of exemplary embodiments of the present disclosure. When the live image which is a moving image configured by the source frame and the trimming image which is a moving image configured by the trimming frame are displayed on the display means side by side, an operator can carry out an operation while referring both images. Therefore, according to the aforementioned configuration, it becomes possible to provide a radiographic imaging device improved to make it easier for an operation to operate.

Effects of the Disclosed Invention According to Exemplary Embodiments

According to exemplary embodiments of the present disclosure, a radiographic imaging device may be provided in which in a moving image displaying an enlarged stent image that appears in a live image, the visibility may be improved by preventing the phenomenon of inverting the stent image. For example, the disclosed invention according to exemplary embodiments is equipped with the editing means that performs editing that a specific one of a plurality of features, which show a position of a stent image that appears in a superimposed frame Fg generated by superimposing source frames F which are sources of the live image VL, is made to be always oriented in the same direction on the frame. By editing a superimposed frame Fg continuously generated by the editing means, an object appears in the edited frame in the same orientation. Therefore, a phenomenon that an object to be display is inverted during the video playback as seen in the past may not occur.

The disclosed invention according to exemplary embodiments may prevent an inversion of an object to be displayed, and therefore is suitable for blood vessel imaging. In the blood vessel imaging, a blood vessel appears in a superimposed frame. When the display of the superimposed frame is inverted like in a conventional configuration, the blood vessel that appears in the superimposed frame is also inverted, the downstream side and the upstream side of the blood vessel that appears in the superimposed frame is inverted. In such a situation, it becomes undistinguishable which side of the superimposed frame is the heart side, making it difficult to perform an operation. According to the present disclosure, sine the display of the superimposed frame is not inverted, the downstream side and the upstream side of the blood vessel that appears in the superimposed frame is not inverted, which results in an easy operation.

BRIEF DESCRIPTION OF THE DRAWINGS

FIG. 16 is a pattern diagram that explains a configuration of a first modified Example of the present disclosure.

FIG. 17 is a pattern diagram that explains a configuration of a first modified Example of the present disclosure.

FIG. 22 is a pattern diagram that explains a configuration of a first modified Example of the present disclosure.

FIG. 23 is a pattern diagram that explains a configuration of a first modified Example of the present disclosure.

DETAILED DESCRIPTION OF THE EMBODIMENTS

Hereinafter, embodiments for carrying out the disclosure will be explained with reference to Examples.

Example 1

Hereinafter, exemplary embodiments of the present disclosure will be explained. The X-ray in Examples corresponds to a radiation of the present disclosure. "FPD" is an abbreviation of a flat panel detector. The X-ray equipment 1 of the present disclosure is for treating angiostenosis. To effectively explain features of the present disclosure, it is appropriate to consider the case in which a stent laid in a blood vessel by a previous operation is observed by a moving image. Therefore, in this Example, this case will be described.

<Overall Configuration of X-Ray Equipment>

Figure 1:
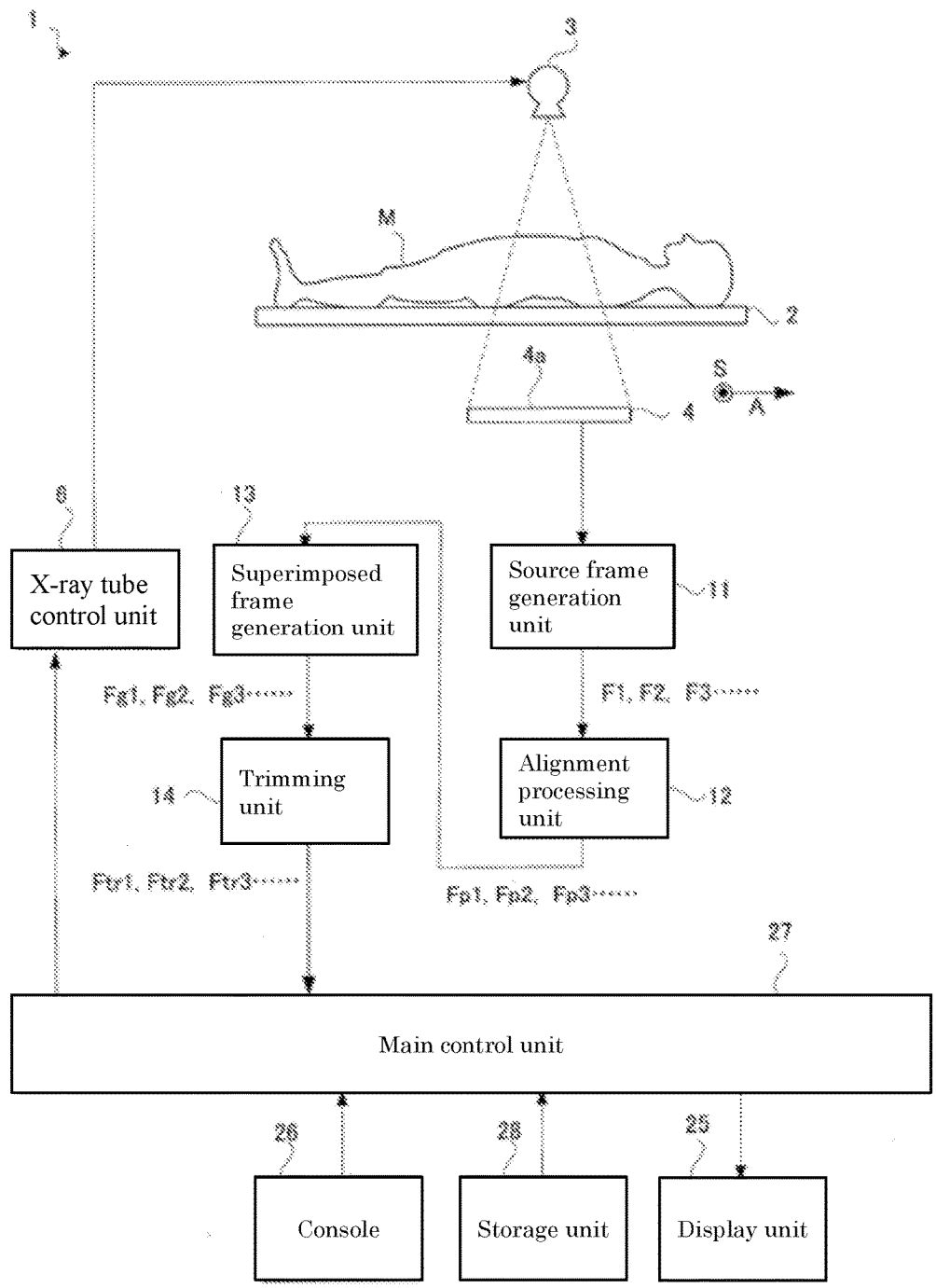
FIG. 1 is a functional block diagram that explains an overall configuration of an X-ray equipment according to Example 1.

Initially, a configuration of an X-ray equipment according to Example 1 will be described. The X-ray equipment 1 is provided with a top board 2 on which a subject M is laid as shown in FIG. 1, an X-ray tube 3 arranged on an upper side of the top plate 2 to irradiate an X-ray toward the subject M, and a FPD arranged on a lower side of the top board 2 to detect the X-ray transmitted through the subject M. The FDA 4 is formed into a rectangular shape having four sides along either the body axis direction A or the body side direction S of the subject M. The X-ray tube 3 irradiates a quadrangular pyramid-shaped X-ray beam expanding radially toward the FPD 4. The FPD 4 is configured to receive the X-ray bean by the entire surface. On the detection surface 4a of the FPD 4 that detects an X-ray, X-ray detection elements are arranged two dimensionally in the body axis direction A and the body side direction S. The X-ray tube 3 corresponds to the radiation source of the present disclosure. The FPD 4 corresponds to the detection means of the present disclosure.

An X-ray tube control unit 6 is provided for the purpose of controlling the X-ray tube 3 by a prescribed tube current, tube voltage, and pulse width. The X-ray tube control unit 6 controls the X-ray tube 3 so as to irradiate an X-ray repeatedly. The FPD 4 detects the X-ray transmitted through the subject M every time the X-ray tube 3 irradiates an X-ray and generates a detection signal. This detection signal is sent to a source frame generation unit 11. The source frame generation unit 11 corresponds to the source frame generation means of the present disclosure.

Figure 2:
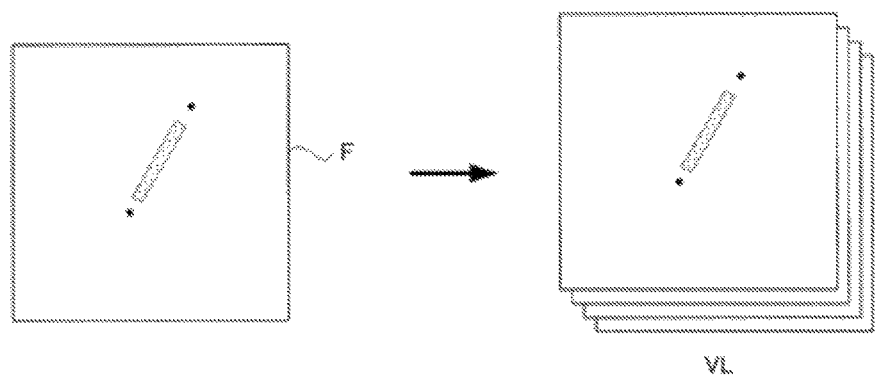
FIG. 2 is a pattern diagram that explains a live image according to Example 1.

The source frame generation unit 11 generates a source frame F which is a source of a moving image based on the detection signal output from the FPD 4. The source frame F denotes one frame configuring a moving image, and therefore the source frame itself is a still image. This source frame F shows a heart of a subject M in whole, and an image of a stent (stent image S) laid in a coronary artery of a subject M by a previous operation appears small as shown in FIG. 2. The moving image configured by the source frame F will be referred to as a live image VL. The live image VL is a moving image showing that a transmission image of the subject M is moving. The source frame generation unit 11 continuously generates a source frame F based on the detection signal sent every irradiation of an X-ray. The stent image S corresponds to the object of the present disclosure.

At both ends of a stent image S in the source frame F and the live image VL, black points as shown in FIG. 2 appear therein. These two black points are stent markers showing positions of the stent in the image. This stent marker is used as a reference when the device performs various kinds of image processing. This stent marker corresponds to the feature point of the present disclosure.

Figure 3:
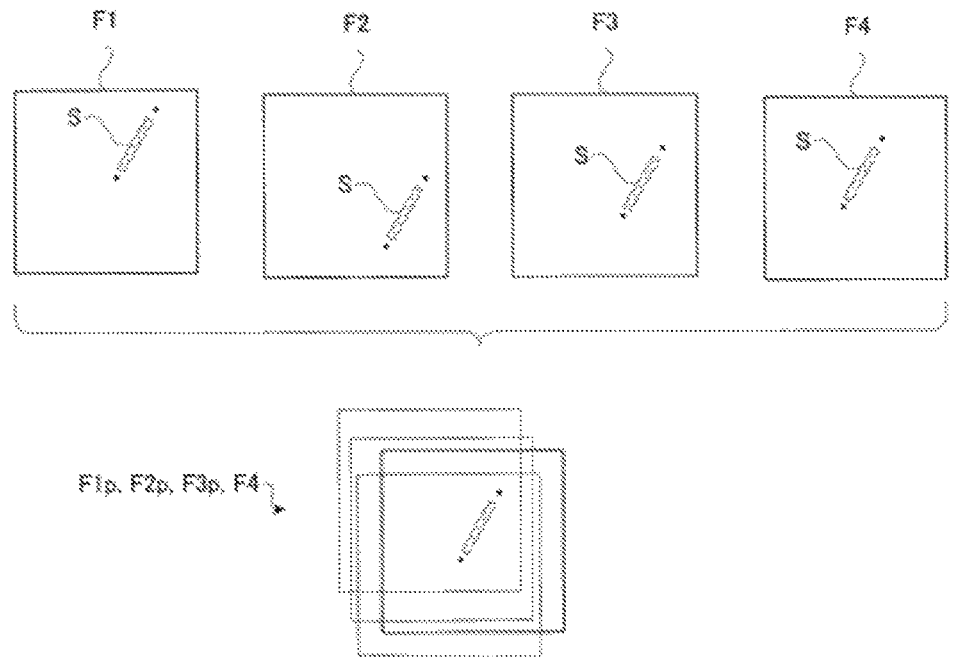
FIG. 3 is a pattern diagram that explains an alignment of a source frame according to Example 1.

Source frames F continuously generated by the source frame generation unit 11 are sent to the alignment processing unit 12. The alignment processing unit 12 recognizes the stent markers existing at both ends of the elongated stent image S that appears in each source frame F. The alignment processing unit 12 aligns source frames so that two same stent markers (corresponding stent markers) that appear in each source frame F are overlapped. For example, the alignment processing unit 12 is configured to specify the positions of the stent markers that appear in each source frame F1, F2, F3, . . . , and relatively move in parallel and rotate each source frame to thereby arrange the position of the stent on each source frame on the same position. The operation of this alignment processing unit 12 will be described. FIG. 3 explains about the parallel movement of each source frame F among operations performed by the alignment processing unit 12. The parallel movement operation of a frame denotes an operation of moving the frame with reference to a reference frame without changing the inclination of the frame. The actual frame is image data, and therefore it is not a nature that the frame may be physically moved in parallel. The parallel movement of the frame denotes a parallel movement that may be realized specifically by data calculation of rewriting the positional data configuring each pixel configuring the frame. The alignment processing unit 12 corresponds to the alignment processing means of the present disclosure.

When the alignment processing unit 12 performs the alignment processing of the four source frames F1, F2, F3, and F4, the source frame F4 photographed most later among source frames F is made as a reference frame. The alignment processing unit 12 calculates the positional difference of the stent markers positioned on both ends of the stent image S that appears in each source frame F with reference to the reference source frame F4, and performs the parallel movement of the source frames F1, F2, and F3 based on the calculated result. In FIG. 3, the source frame F after the parallel movement is denoted as symbols F1$p$, F2$p$, and F3$p$.

By this parallel movements, the positions that stent images S appear in the source frames F1, F2, and F3 are changed so that the positions match a position that the stent image S on the source frame F4 appears.

Figure 4:
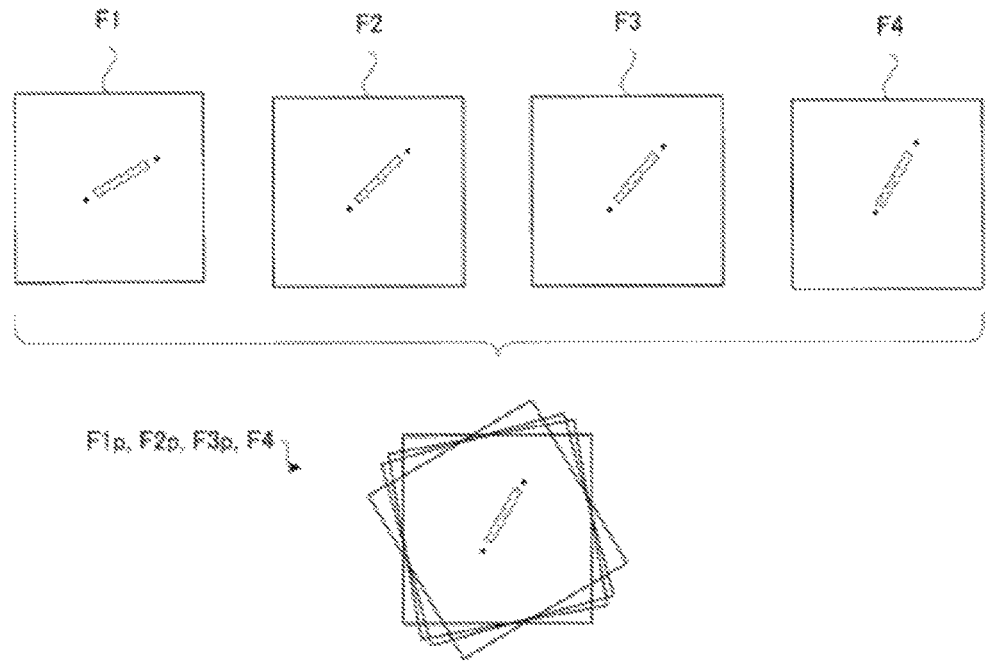
FIG. 4 is a pattern diagram that explains an alignment of a source frame according to Example 1.

FIG. 4 explains about a rotation of each source frame F among operations performed by the alignment processing unit 12. The rotational movement of a frame denotes an operation of rotating the frame with reference to a reference frame without changing the position of the center of gravity of the frame. The actual frame is image data, and therefore it is not a nature that the frame may be physically rotated. The rotation of the frame denotes a rotational movement that may be realized specifically by data calculation of rewriting the positional data configuring each pixel configuring the frame.

When the alignment processing unit 12 performs the alignment processing of the four source frames F1, F2, F3, and F4, the source frame F4 photographed most later among source frames F is made as a reference frame. The alignment processing unit 12 calculates to what extent the stent marker image of the stent image S that appears in each source frame F with reference to the reference source frame F4 is rotated, and performs rotations of the source frames F1, F2, and F3 based on the calculated result. In FIG. 4, the source frames F after rotations are denoted as symbols F1$p$, F2$p$, and F3$p$.

By this rotation, the inclination of the stent images S that appears in the source frame F1, F2, and F3 is changed so that the inclination matches the inclination of the stent image S that appears in the source frame F4.

The actual alignment processing unit 12 executes the parallel movement and the rotation of the source frame F1, F2, and F3 in the same processing. The alignment processing unit 12 performs an image analysis of each frame to calculate the positions of both ends of the stent image S on each frame. The stent is provided with stent markers that hardly allow penetration of an X-ray at both ends, and therefore the positions of both ends of the stent in each frame may be calculated easily. Even in the case of a stent not provided with stent markers, the positions of both ends of the stent in each frame may be calculated relatively easily by the extraction processing of feature points. A stent contains metal or the like, and therefore a stent itself has a nature that hardly allows penetration of an X-ray. For this reason, a stent appears clearly in each frame to some extent.

The alignment processing unit 12 obtains the positon and the inclination angle of a segment connecting both ends of the stent image S from the calculation result of the positions of both ends of the stent image S that appear in each frame, and calculates to what extent they differ between the source frame F4 and other source frames F1, F2, and F3. The alignment processing unit 12 makes the source frame F1, F2, and F3 move in parallel and rotate with reference to the source frame F4.

Figure 5:
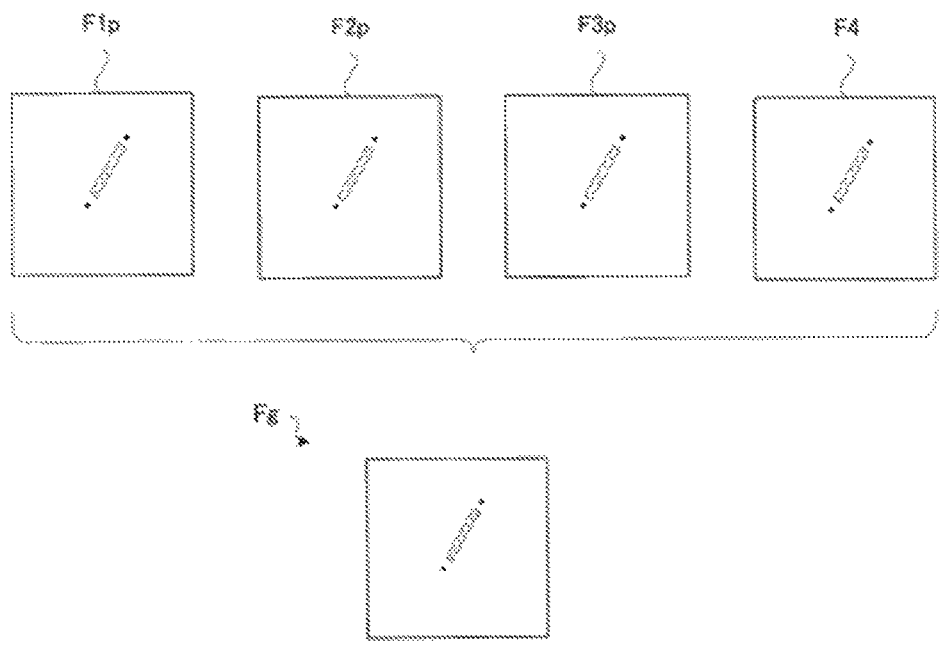
FIG. 5 is a pattern diagram that explains a generation of a superimposed frame according to Example 1.

The calculation results of the alignment processing unit 12 is sent to the superimposed frame generation unit 13. The superimposed frame generation unit 13 superimposes source frames F subjected to the alignment processing to repeatedly generate a superimposed frame Fg in which images of objects (stent images S) are superimposed. For example, the superimposed frame generation unit 13 superimposes four frames including the source frame F4 and the aligned source frames F1$p$, F2$p$, F3$p$ as shown in FIG. 5 to generate a superimposed frame Fg1 of the source frame F1. In each of the source frames F1$p$, F2$p$, F3$p$, and F4$p$, stent image S having the same inclination appears at the same position. Therefore, in the superimposed frame Fg1, a stent image S in which four stent images S appearing in source frames F are overlapped appears. This stent image S is improved in S/N ratio than the stent image S in the source frame F and superior in visibility. The superimposed frame generation unit 13 corresponds to the superimposed frame generation means of the present disclosure.

Figure 6:
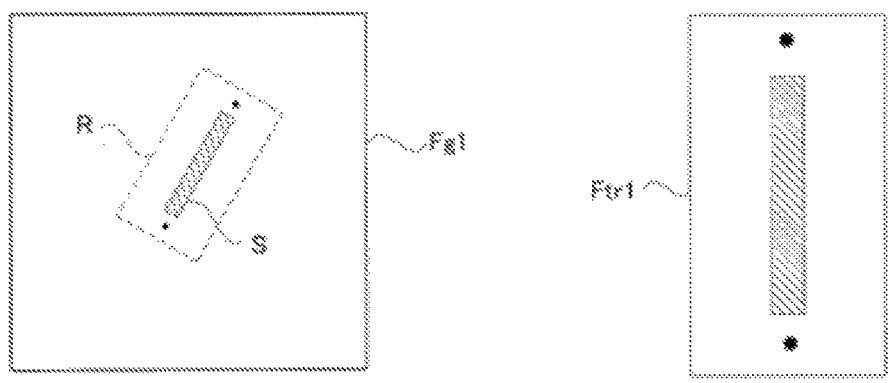
FIG. 6 is a pattern diagram that explains a generation of a trimming frame according to Example 1.

The superimposed frame Fg1 is sent to a trimming unit 14. The trimming unit 14 performs an image analysis of the superimposed frame Fg1 to recognize the positions of both ends of the stent image S in the superimposed frame Fg1. Then, as shown on the left side of FIG. 6, the trimming unit 14 sets a rectangular region R on the superimposed frame Fg1 so as to surround the stent image S. This rectangular region R has an elongated shape in the direction that the elongated stent image S extends and is inclined by the same angle as the stent image S. The rectangular region R is set so that the stent image S is positioned at the center of the rectangular region R. The positions of both ends of the stent image S that appear in the superimposed frame Fg1 may be obtained relatively easily by an image analysis as explained about the aforementioned alignment processing unit 12. As the image analysis used in this case, specifically, a feature point extraction method by edge enhancing processing may be exemplified. The trimming unit 14 corresponds to the editing means of the present disclosure.

The trimming unit 14 performs trimming processing of extracting the rectangular region R against the superimposed frame Fg1, and makes the taken-out rectangular region R independent as a new trimming frame Ftr1. As described above, the trimming unit 14 repeatedly generates a trimming frame Ftr every superimposed frame Fg by recognizing both ends of an elongated object (stent image S) that appears in each superimposed frame and subjecting each superimposed frame Fg to the trimming processing so as to remain a rectangular region including an image of the object. At this time, it is required to cancel the inclination of the rectangular region R inclined along the inclination orientation shown on the left side of FIG. 6 to thereby generate a trimming frame Ftr1 that appears so that the stent image S as shown on the right side of FIG. 6 extends up and down of the image. At this time, it becomes a problem which part of the region R should be set as the upper side of the trimming frame Ftr1. The trimming unit 14 is required to generate a frame by deciding the orientation of the trimming frame Ftr1.

<Most Characteristic Configuration of the Present Disclosure>

Here, the most characteristic configuration of the present disclosure will be described. The trimming unit 14 of the present disclosure is characterized in how to determine the orientation of the trimming frame Ftr1. For example, the trimming unit 14 determines the orientation of the trimming frame Ftr1 by one of three modes. The three modes include an upper and lower reference mode MV, a left and right reference mode MH, and a stent marker specification mode, and an operator can select one mode among these three modes. The trimming unit 14 operates in one of modes based on the mode selection by the operator.

<Upper and Lower Reference Mode MV>

Figure 7:
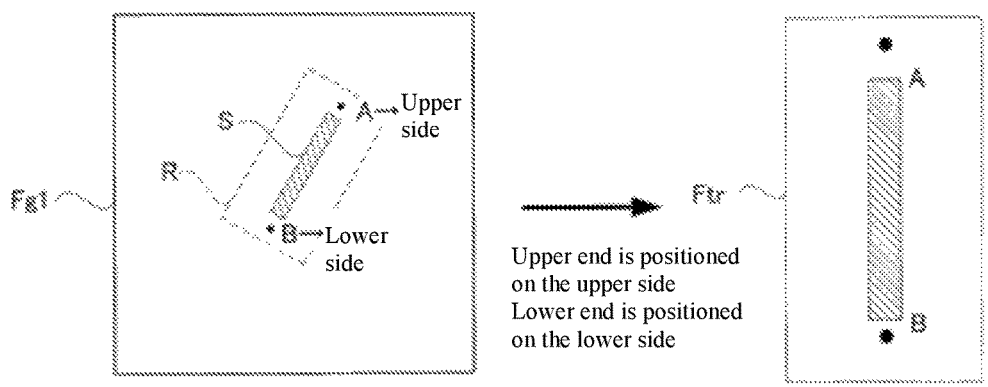
FIG. 7 is a pattern diagram that explains an upper and lower reference mode according to Example 1.

An upper and lower reference mode MV which is one of methods that the trimming unit 14 determines the orientation of the trimming frame Ftr1 will be explained. FIG. 7 shows a procedure in which the trimming unit 14 operates in this mode. The trimming unit 14 judges which end among both ends A and B of the stent image S that appears in the region R in the superimposed frame Fg1 is positioned on the upper side and on the lower side. In the case shown in FIG. 7, in the superimposed frame Fg1, the end of the stent positioned on the upper side is the end A, and the end of the stent positioned on the lower side is the end B. The trimming unit 14 determines the orientation of the trimming frame Ftr1 so that the upper side end A is positioned on the upper side of the trimming frame Ftr1 and the lower side end B is positioned on the lower side of the trimming frame Ftr1. Thus, a vertically long trimming frame Ftr1 is generated. This upper and lower reference mode MV is a mode for deciding the orientation of the trimming frame Ftr by determining the upper end and the lower end of the stent appear on which side among upper, lower, left and right sides of the trimming frame Ftr based on the stent marker image that appears in the superimposed frame Fg.

<Left and Right Reference Mode MH>

Figure 8:
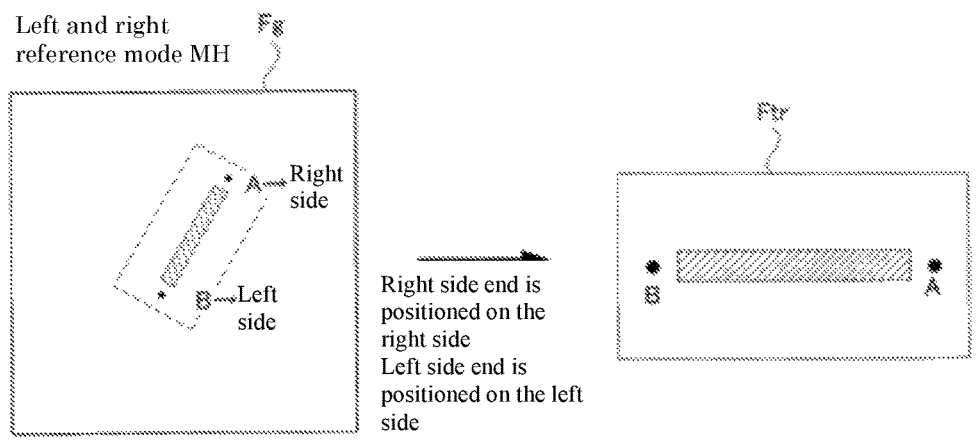
FIG. 8 is a pattern diagram that explains a left and right reference mode according to Example 1.

A left and right reference mode MH which is one of methods that the trimming unit 14 determines the orientation of the trimming frame Ftr1 will be explained. FIG. 8 shows a procedure in which the trimming unit 14 operates in this mode. The trimming unit 14 judges which end among both ends A and B of the stent image S that appears in the region R in the superimposed frame Fg1 is positioned on the right side and the left side. In the case shown in FIG. 8, in the superimposed frame Fg1, the end of the stent positioned on the right side is the end A, and the end of the stent positioned on the left side is the end B. The trimming unit 14 determines the orientation of the trimming frame Ftr1 so that the right end A is positioned on the right side of the trimming frame Ftr1 and the left end B is positioned on the left side of the trimming frame Ftr1. Thus, a horizontally long trimming frame Ftr1 is generated. This left and right reference mode MH is a mode that determines the orientation of the trimming frame Ftr by determining that the right end and left end of the stent appears which of the upper, lower, left, and right side of the trimming frame Ftr based on the stent marker image that appears in the superimposed frame Fg.

Figure 9:
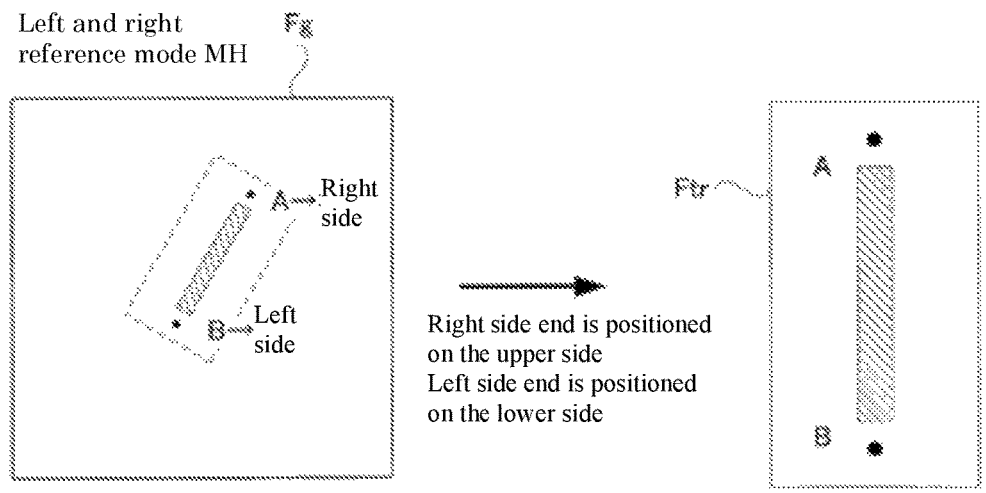
FIG. 9 is a pattern diagram that explains a left and right reference mode according to Example 1.

In a state in which the aforementioned left and right reference mode is selected, the trimming unit 14 may be performed as follows. FIG. 9 show a procedure in which the trimming unit 14 operates in the left and right reference mode MH which is different from the mode shown in FIG. 8. The trimming unit 14 judges that both ends A and B of the stent image S that appear in the region R in the superimposed frame Fg1 are positioned which sides, i.e., the right side or the left side. In the case shown in FIG. 9, in the superimposed frame Fg1, the end positioned on the right side in the frame is the end A, and the end positioned on the left side is the end B. So far, the above explanation is the same as in FIG. 8. The trimming unit 14 determines the orientation of the trimming frame Ftr1 so that the right end A is positioned on the upper side of the trimming frame Ftr1 and the left end B is positioned on the lower side of the trimming frame Ftr1. Thus, different from FIG. 8, a vertically long trimming frame Ftr1 is generated.

<Stent Marker Specification Mode>

The following description is directed to a stent marker specification mode which is one of methods that the trimming unit 14 determines the orientation of the trimming frame Ftr1. This is configured such that an operator selects any one of stent marker images that appear in the currently displayed trimming frame and the selected stent marker may always be displayed on the upper or lower side of the trimming frame. The trimming frame in which an operator selects the stent marker may not be limited to a currently displayed trimming frame, but may be a previously displayed trimming frame. For example, for the purpose of making the display unit 25 select a stent marker, a previous trimming frame is displayed on another window. The selection of a stent marker may be performed by a mouse or a keyboard attached to the console 26, and also may be performed by a touch panel attached to the console 26. It is possible for an operator to display the selected stent marker on which side of the trimming frame by an operation of the console 26.

Therefore, according to this mode, the generation of the trimming frame may be performed by the same method as a method of a conventional device or in the aforementioned upper and lower reference mode MV or the left and right reference mode MH. After selecting a stent marker image, the display of the display unit 25 shifts to a stent marker specification mode.

In the case of generating a trimming frame in a stent marker specification mode, it is necessary to determine which of two stent maker images that appear in a superimposed frame Fg which becomes a source frame is one specified by an operator. How the determination is performed will be explained as follows. Trimming frames used at the time of selecting a stent marker include a source superimposed frame. This superimposed frame will be referred to as a reference superimposed frame. After the selection by an operator, it is supposed that a superimposed frame is newly obtained. A case in which a trimming frame is generated based on this new superimposed frame will be considered as follows. In both the reference superimposed frame and the new superimposed frame, two stent maker images appear. Among them, one of stent markers that appear in the reference superimposed frame and is selected by an operator is denoted as A, and the other of stent images not selected by the operation is denoted as B. There is no difference between both the superimposed frames in which the same stent markers appears, but there is a different between the appearance positions of both the stent markers.

One of stent markers that appears in the new superimposed frame should be A, and the other should be B. The trimming unit 14 presumes two cases, i.e., a case in which one of stent markers that appears in the new superimposed frame is A and the other is B, and a case in which one of stent markers that appears in the new superimposed frame is B and the other is A. The trimming unit 14 selects one of the cases in which it is possible to realize by less movement of the stent marker on the reference superimposed frame by calculating the total moving distance of the stent marker A, B in each presumed case. Then, the trimming unit 14 specifies the stent marker that appears in the new superimposed frame based on the selected presumption, and determines the orientation of the trimming frame based on the result.

The trimming unit 14 repeatedly generates a trimming frame Ftr on each superimposed frame Fg while deciding the orientation of the trimming frame Ftr in accordance with the mode selection made by an operator. For example, in the case in which the left and right reference mode MH explained with reference to FIG. 9 is selected, the trimming unit 14 determines the orientation of the trimming frame Ftr so that the right end of an object appeared in the superimposed frame Fg is positioned on the right end of the trimming frame Ftr and the left end of the object appeared in the superimposed frame Fg is positioned on the left end of the trimming frame Ftr.

As described above, the trimming unit 14 generates a trimming frame Ftr by repeatedly performing editing of making a specified stent marker among stent markers appeared in superimposed frames generated repeatedly point always the same orientation in a frame on each superimposed frame Fg. At this time, the trimming unit 14 determines a stent marker which becomes an editing reference among stent markers that appear in a superimposed frame Fg based on a positional relationship of stent markers or an instruction of an operator.

<Effects of the Present Disclosure>

As described above, by configuring that three modes may be selected regarding the determination of the orientation of the trimming frame Ftr1, it becomes easy to visually recognize the trimming image VT which is a moving image constituted by a trimming frame Ftr. Therefore, this will be explained.

Initially, a trimming image VT will be explained. A trimming image VT denotes a moving image which is configured by trimming frames Ftr which are generated continuously. The aforementioned superimposed frame Fg1 according to FIG. 3, FIG. 4, and FIG. 5 is, in reality, repeated every time a source frame F is newly generated. The trimming frame Ftr is also repeatedly generated every time a superimposed frame Fg is generated, and therefore a trimming frame Ftr is repeatedly generated until the generation of a source frame F is stopped. The trimming image VT is a moving image generated by combining obtained trimming frames Ftr in chronological order, and also is a moving image showing that a stent image S or a peripheral portion of a stent image S changes.

Figure 10:
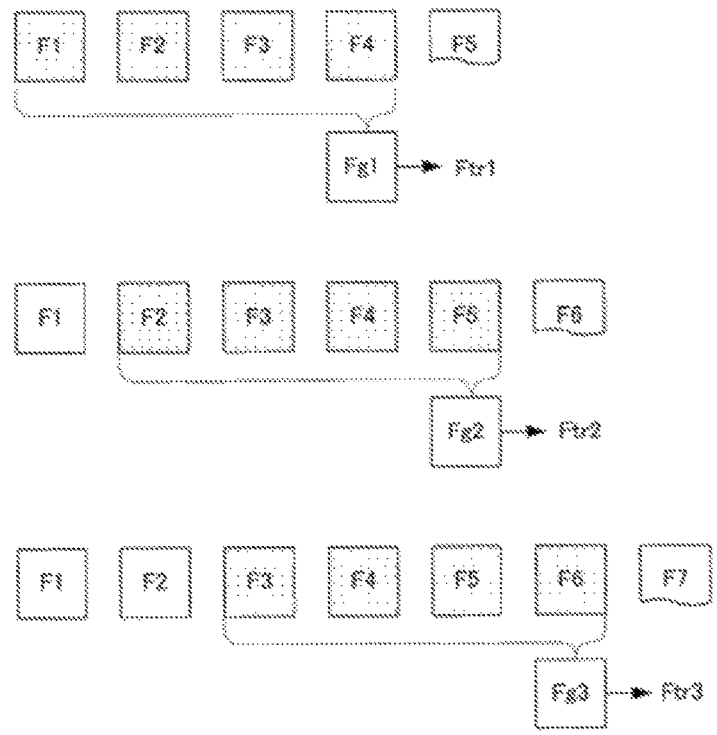
FIG. 10 is a pattern diagram that explains procedures in which each frame is being generated with time according to Example 1.

FIG. 10 is a drawing that explains a generation method of a trimming image VT. It is assumed that source frames are continuously generated in the order of F1, F2, F3, F4, F5, F6, and F7. The upper part of FIG. 10 shows a time point when source frames have been generated up to the source frame F4, and the source frame F5 is being generated. At this time point, a superimposed frame Fg1 is generated by superimposing the source frames F1, F2, F3, and F4. A trimming frame Ftr1 is generated by subjecting the superimposed frame Fg1 to trimming processing. In FIG. 10, it is explained that the superimposed frame Fg1 is generated by overlapping four source frames F. By explaining in this manner, it is made to ensure the consistency with the explanation with reference to FIG. 2, FIG. 3, FIG. 4, and FIG. 5 in which the superimposed frame is generated by superimposing four source frames F in the same manner as in the above case. The orientation of the stent image S that appears in the superimposed frame Fg1 depends on the orientation of the stent image S in the most recent source frame F4 when the superimposed frame Fg1 is generated.

Further, the middle part of FIG. 10 shows a time point when source frames have been generated up to the source frame F5, and the source frame F6 is being generated. At this time point, a superimposed frame Fg2 is generated by superimposing the source frames F2, F3, F4, and F5. A trimming frame Ftr2 is generated by subjecting the superimposed frame Fg2 to trimming processing. The orientation of the stent image S that appears in the superimposed frame Fg2 depends on the orientation of the stent image S in the most recent source frame F5 when the superimposed frame Fg1 is generated.

Further, the lower part of FIG. 10 shows a time point when source frames have been generated up to the source frame F6, and the source frame F7 is being generated. At this time point, a superimposed frame Fg3 is generated by superimposing the four source frames F3, F4, F5, and F6. A trimming frame Ftr3 is generated by subjecting the superimposed frame Fg3 to trimming processing. The orientation of the stent image S that appears in the superimposed frame Fg3 depends on the orientation of the stent image S in the most recent source frame F6 when the superimposed frame Fg1 is generated.

As described above, the superimposed frame generation unit 13 continuously generates a superimposed frame Fg by superimposing most recently photographed four source frames F. The trimming unit 14 generates a trimming frame Ftr by subjecting the most recently generated one superimposed frame Fg1 to trimming processing.

Subsequently, how to select the upper and lower reference mode MV and the left and right reference mode MH will be explained. According to the present disclosure, it is configured such that an operator can select a mode appropriate to a stent image S that appears in a superimposed frame Fg. A specific example of a stent image S in which the upper and lower reference mode MV is advantageous and a specific example of a stent image S in which the left and right reference mode MH is advantageous will be explained.

<Case in which Upper and Lower Reference Mode MV is Advantageous>

Figure 11:
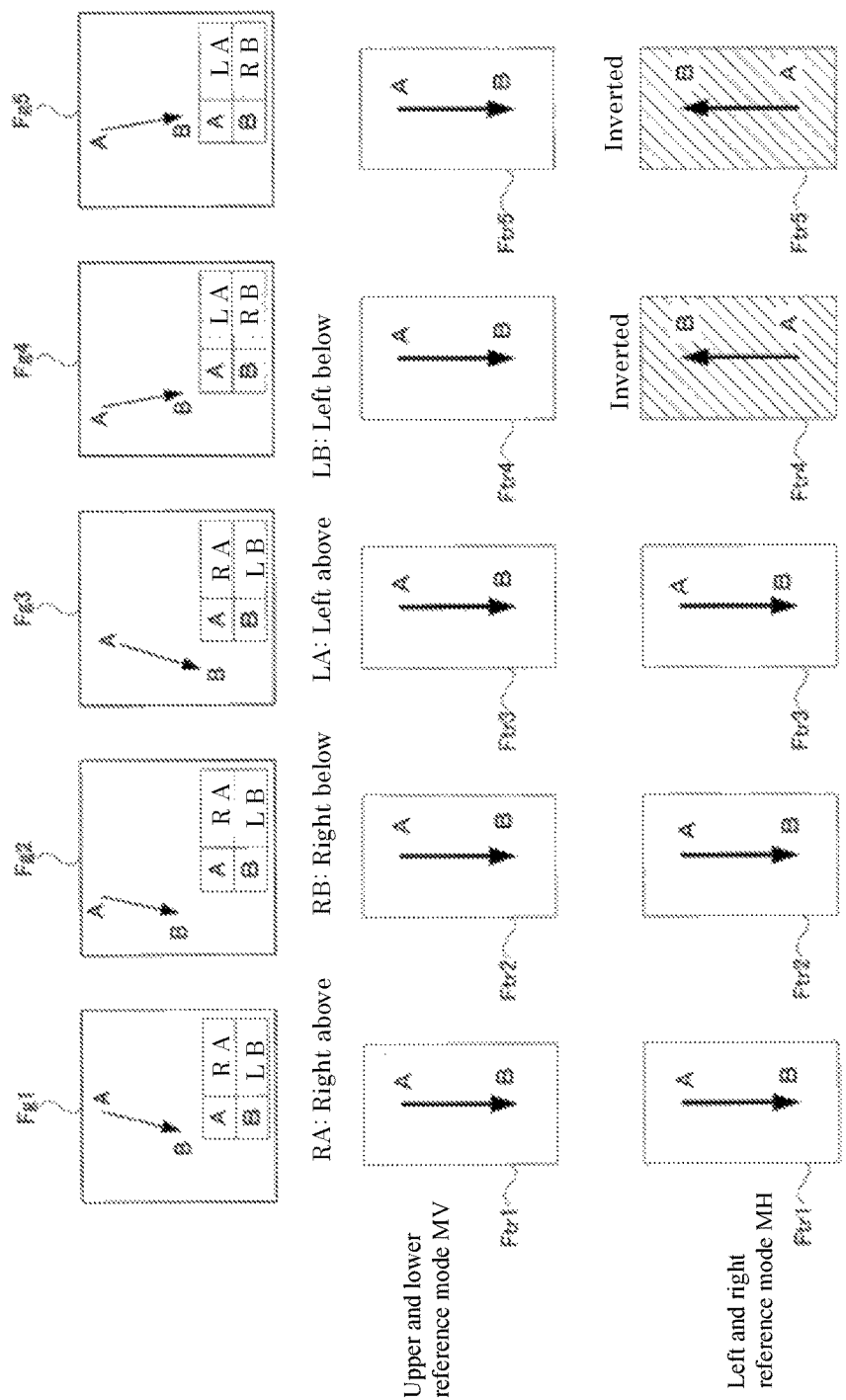
FIG. 11 is a pattern diagram that explains an effectiveness of an upper and lower reference mode according to Example 1.

FIG. 11 explains a stent image S in which the upper and lower reference mode MV is advantageous. As shown in the upper portion of FIG. 11, in cases where a stent image S is appeared in a vertical orientation in each of superimposed frames Fg1 to Fg5, it is advantageous to generate trimming frames Ftr1 to Ftr5 in accordance with the upper and lower reference mode MV. The reason will be explained. In cases where a stent image S is appeared in a vertical orientation in each of superimposed frames Fg1 to Fg5, both ends of the stent image S appear slightly different in orientation among superimposed frames Fg1 to Fg5. However, the positions of both ends of the stent do not invert upside down. For example, in all of the superimposed frames Fg1 to Fg5, the end A of the stent image S may always be positioned on the upper side, and the end B of the stent image S may always be positioned on the lower side.

The trimming unit 14 in the case in which the upper and lower reference mode MV is selected determines the orientation of the trimming frame Ftr so that the upper end of an object appeared in the superimposed frame Fg is positioned on the upper end of the trimming frame Ftr and the lower end of the object appeared in the superimposed frame Fg is positioned on the lower end of the trimming frame Ftr.

Therefore, according to the upper and lower reference mode MV, the orientation of the frame is determined so that of both ends A and B appeared in the superimposed frame Fg1 to Fg5, the upper side end is positioned on the upper side ant that the lower side is positioned on the lower side. Thus, in the trimming frames Ftr1 to Ftr5 generated in the upper and lower reference mode MV, as shown in the middle of FIG. 11, the end of the stent image S may always be positioned on the upper side, and the end B is positioned on the lower side. For example, in the trimming image VT to be generated based on the trimming frame Ftr1 to Ftr5, the stent image S does not invert.

On the other hand, according to the left and right reference mode MH, the orientation of the frame is determined so that of both ends A and B appeared in the superimposed frame Fg1 to Fg5, the right side end is positioned, for example, on the upper side ant that the lower side is positioned, for example, on the lower side. Referring to the upper portion of FIG. 11, in the superimposed frames Fg1 to Fg3, the end A is positioned on the right side and the end B is positioned on the left side, while in the superimposed frames Fg4 and Fg5, the positions of the end A and the end B are changed such that the end A is positioned on the left side and the end B is positioned on the right side. As described above, in cases where stent images S appear in superimposed frames Fg in a vertical orientation, the relationship between the right end and the left end of the stent image S is likely to be inverted. A slight inclination of a stent image S in the superimposed frame Fg causes easy collapse of the relationship of which end of the stent image S being on the left side or the right side.

Therefore, in the trimming frames Ftr1 to Ftr3 generated in the left and right reference mode MH, as shown in the lower portion of FIG. 11, the stent image S appears so that the end A is positioned on the upper side and the end B is positioned on the lower side. On the other hand, in the trimming frames Ftr4 and Ftr5, the stent images S appear so that the end A is positioned on the lower side and the end B is positioned on the lower side. For example, in the trimming image VT to be generated based on the trimming frames Ftr1 to Ftr5, the stent image S is sometimes reverted.

As described above, in cases where a stent image S appears in a vertical orientation in each of superimposed frames Fg1 to Fg2, it is advantageous to generate trimming frames Ftr1 to Ftr5 in accordance with the upper and lower reference mode MV. This is because some stent images S in the trimming frames Ftr1 to Ftr5 are not reverted.

<Case in which Left and Right Reference Mode MH is Advantageous>

Figure 12:
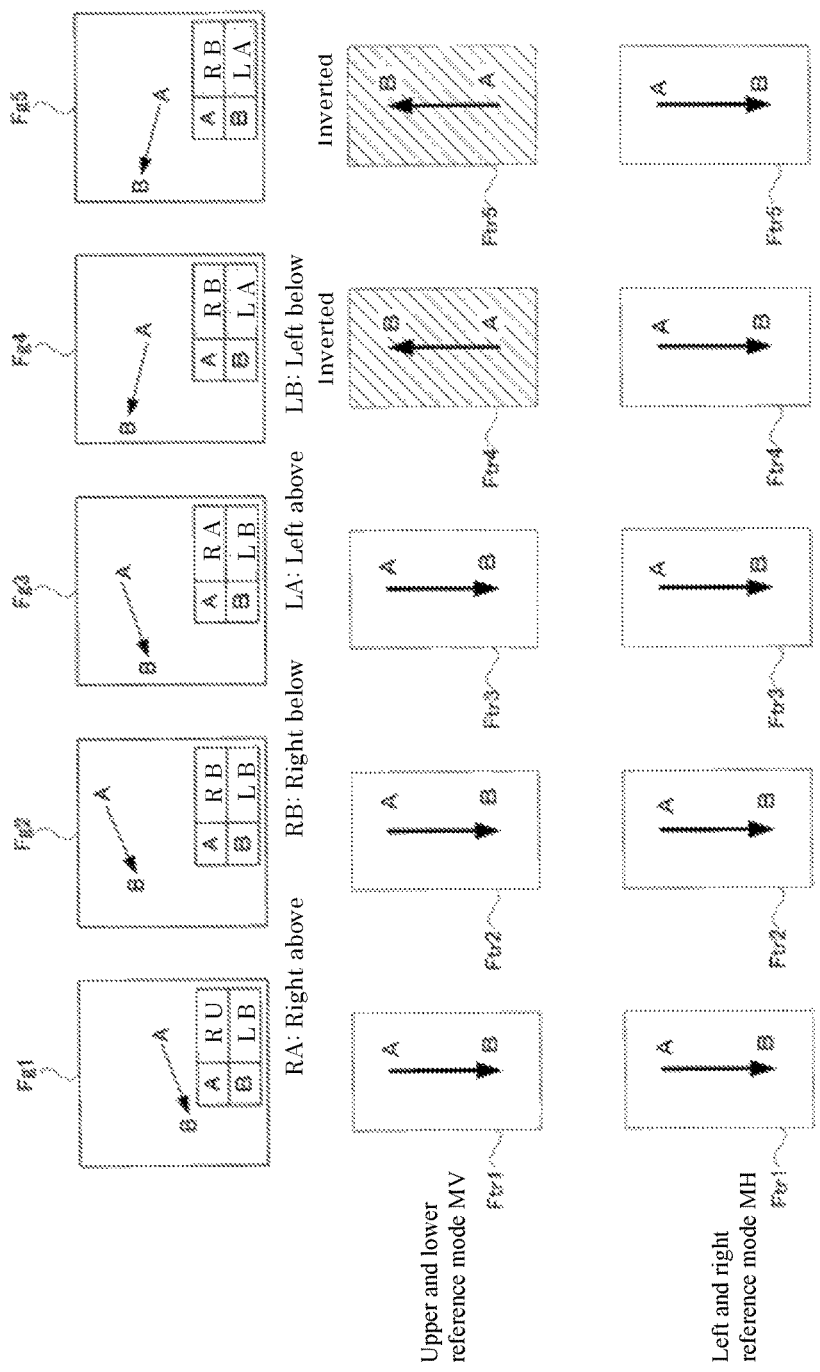
FIG. 12 is a pattern diagram that explains an effectiveness of a left and right reference mode according to Example 1.

FIG. 12 explains a stent image S in which the left and right reference mode MH is advantageous. As shown in the upper portion of FIG. 12, in cases where a stent image S appears in a horizontal orientation in each of superimposed frames Fg1 to Fg5, it is advantageous to generate trimming frames Ftr1 to Ftr5 in accordance with the left and right reference mode MH. The reason is the same as in the case in which the aforementioned upper and lower reference mode is appropriate to a vertically oriented stent image S. In cases where a stent image S is appeared in a horizontal orientation in each of superimposed frames Fg1 to Fg5, both ends of the stent image S appear slightly different in orientation among superimposed frames Fg1 to Fg5. However, the positions of both ends of the stent do not invert left and right. For example, in all of the superimposed frames Fg1 to Fg5, the end A of the stent image S may always be positioned on the right side, and the end B of the stent image S may always be positioned on the left side.

The trimming unit 14 in the case in which the left and right reference mode MH is selected determines the orientation of the trimming frame Ftr so that the right end of an object appeared in the superimposed frame Fg is positioned on the upper end of the trimming frame Ftr and the left end of the object appeared in the superimposed frame Fg is positioned on the lower end of the trimming frame Ftr.

Therefore, according to the left and right reference mode MH, the orientation of the frame is determined so that of both ends A and B appeared in the superimposed frame Fg1 to Fg5, the right side end is positioned, for example, on the upper side ant that the lower side is positioned, for example, on the lower side. Thus, in the trimming frames Ftr1 to Ftr5 generated in the left and right reference mode MH, as shown in the lower portion of FIG. 12, the end A of the stent image S may always be positioned on the upper side, and the end B may always be positioned on the lower side. For example, in the trimming image VT to be generated based on the trimming frame Ftr1 to Ftr5, the stent image S does not invert.

On the other hand, according to the upper and lower reference mode MV, the orientation of the frame is determined so that of both ends A and B appeared in the superimposed frame Fg1 to Fg5, the upper side end is positioned on the upper side and that the lower side is positioned on the lower side. Referring to the upper portion of FIG. 12, in the superimposed frames Fg1 to Fg3, the end A is positioned on the upper side and the end B is positioned on the lower, while in the superimposed frames Fg4 and Fg5, the positions of the end A and the end B are changed such that the end A is positioned on the lower and the end B is positioned on the upper side. As described above, in cases where stent images S appear in superimposed frames Fg in a horizontal orientation, the relationship between the upper end and the lower end of the stent image S is likely to be inverted. A slight inclination of a stent image S in the superimposed frame Fg causes easy collapse of the relationship of which end of the stent image S being on the upper side or the lower side.

Therefore, in the trimming frames Ftr1 to Ftr3 generated in the upper and lower reference mode MV, as shown in the middle portion of FIG. 12, the stent image S appears so that the end A is positioned on the upper side and the end B is positioned on the lower side. On the other hand, in the trimming frames Ftr4 and Ftr5, the stent images S appear so that the end A is positioned on the lower side and the end B is positioned on the lower side. For example, in the trimming image VT to be generated based on the trimming frames Ftr1 to Ftr5, the stent image S is sometimes inverted.

As described above, in cases where a stent image S is appeared in a horizontal orientation in each of superimposed frames Fg1 to Fg5, it is advantageous to generate trimming frames Ftr1 to Ftr5 in accordance with the left and right reference mode MH. This is because some stent images S in the trimming frames Ftr1 to Ftr5 are not inverted.

In cases where the orientation of a stent image S in a superimposed frame Fg is an intermediate inclination (inclination of 45 degrees) between a vertical orientation and a horizontal orientation, both modes are suitable for taking a trimming image. In FIGS. 11 and 12, the stent is illustrated as an arrow, which is for convenience of explanation. The actual stent image S is a bar-shaped image.

<Other Configuration of X-Ray Equipment>

Other configuration of the X-ray equipment will be explained. The display unit 25 is provided for the purpose of displaying each image acquired by an X-ray photography. The console 26 is provided for the purpose of inputting an instruction of initiation of an X-ray irradiation by an operator and/or an operator's selection for selecting one of the aforementioned three modes. Further, a main control unit 27 is provided for the purpose of comprehensively controlling each control unit. This main control unit 27 is configured by a CPU, and the X-ray tube control unit 6 and each unit 11, 12, 13, and 14 are realized by executing various programs. The aforementioned each unit may be executed by a separate arithmetic device in charge of each unit. A storage unit 28 stores all of parameters used for image processing and parameters on a control of the X-ray equipment 1 for an intermediate image or the like to be generated by image processing. A display unit 25 corresponds to the display means of the present disclosure, and the console 26 corresponds to the input means of the present disclosure.

<Operation of X-Ray Equipment>

Figure 13:
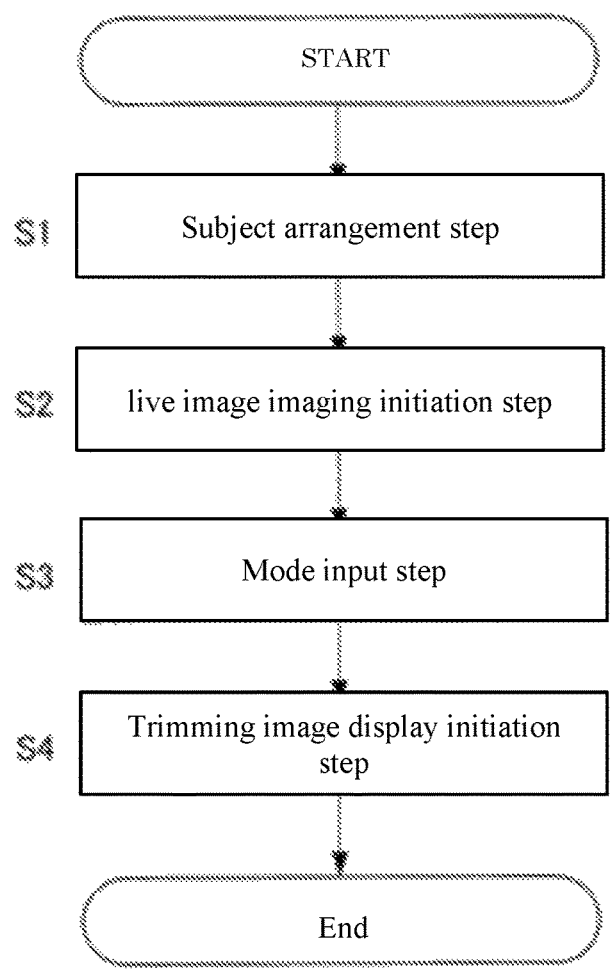
FIG. 13 is a flowchart that explains an operation of an X-ray equipment according to Example 1.

Now, the operation of the X-ray equipment of Example 1 will be explained with reference to the flowchart shown in FIG. 13. In imaging a subject M with the X-ray equipment according to Example 1, initially, a subject M is arranged on the top board 2 (Subject Arrangement Step S1). When an operator gives an instruction to initiate imaging of a live image VL to the device via the console 26, the X-ray tube control unit 6 makes the X-ray tube 3 initiate irradiation of an X-ray (Live Image Imaging Initiation Step S2). At this time, an X-ray to be irradiated is irradiated in a continuous manner or in a repeated pulse manner. The display unit 25 continuously displays the most recent source frame F, and displays an X-ray image as a moving image to an operation. The moving image displayed at this time is a live image VL. It is assumed that the stent image S in a subject appears in the live image VL. The left side of FIG. 14 shows a state in which a live image VL appears in the display unit 25.

The stent image S appears in the live image VL in a small and blurred manner, and moves around in the live image VL. Therefore, an operator judges that it is necessary to visually recognize the stent image S more accurately, and gives an instruction to display a trimming image VT to the device. Then, the console 26 makes the attached operation panel display a display that allows an operator to select which mode of the upper and lower reference mode MV and the left and right reference mode MH is used to generate a trimming frame Ftr. The operator selects one of three modes, the upper and lower reference mode MV, the left and right reference mode MH, and the stent marker specification mode, and inputs the selection result to the device via the console 26 (Mode Input Step S3).

Figure 14:
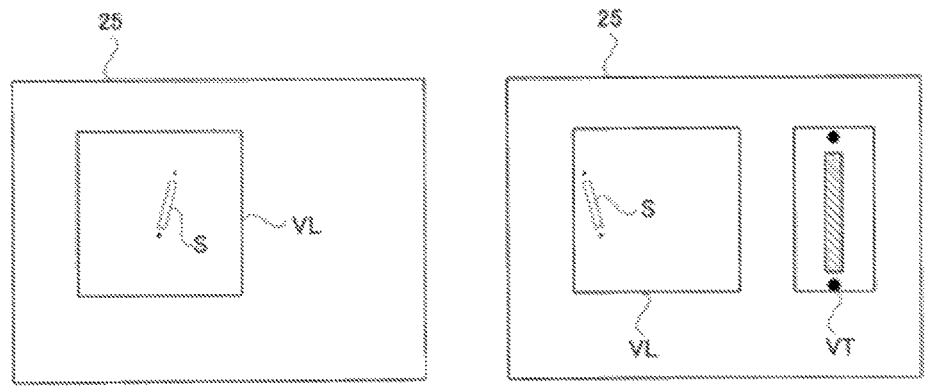
FIG. 14 is a pattern diagram that explains a display unit according to Example 1.

In the case shown on the left side of FIG. 14, the stent image S in the live image VL is oriented in the vertical direction, and therefore when the upper and lower reference mode MV is selected, the inversion of the stent image S in the trimming image VT is less likely to occur and therefore it is advantageous for an accurate observation of a stent image S. In cases where the stent image S in the live image VL is oriented in the horizontal direction, when the left and right reference mode MH is selected rather than selecting the upper and lower reference mode MV, the inversion of the stent image S in the trimming image VT is less likely to occur and therefore it is advantageous for an accurate observation of a stent image S.

When an operator inputs a selection of the left and right reference mode MH via the console 26, the generation of the superimposed frame Fg and the generation of the trimming frame Ftr accompanied by the generation of the superimposed frame Fg are initiated, and this is displayed on the display unit 25 (Trimming Image Display Initiation Step S4). At this time, the trimming unit 14 determines the orientation of the trimming frame Ftr in accordance with the mode selected by the operator. The trimming frame Ftr is continuously generated during which the source frame F is kept being generated. The orientation of each of these trimming frames Ftr is determined in accordance with the mode selected by the operator. The display unit 25 continuously displays the most recent trimming frame Ftr, and displays a stent image S as a moving image to the operation. The moving image displayed at this time is a trimming image VT. The trimming image VT is a moving image in which a stent image S appears in the center. Therefore, in the trimming image VT, the shape change such as bending of the stent image S may be seen, or the change of the blood vessel image around the stent image S may be seen.

The right side of FIG. 14 shows a state in which a trimming image VT appears in the display unit 25. As shown in the right side of FIG. 14, the display unit 25 keeps showing the display of the live image VL since the live image imaging initiation step S2. In displaying the trimming image VT, the display unit 25 additionally displays the trimming image VT and the live image VL in a state in which the trimming image and the live image are not overlapped. The live image VL and the trimming image VT show the state of the X-ray image at the same time point (current). However, the generation of the trimming frame Ftr requires a plurality of source frames F, and the trimming frame may not be generated only by the most recent source frame F. For this reason, the trimming image VT is an image in which a past stent image S is overlapped on the current stent image S. However, since stent images S appear in source frames F close in the photographed time in a similar shape, it may be handled that almost current stent image S appears.

As described above, the display unit 25 displays a live image VL which is a moving image configured by a source frame F and a trimming image VT which is a moving image configured by a moving image which is configured by a trimming frame Ftr improved in S/N ratio by superimposing frames side by side. At this time, the display unit 25 displays an enlarged view of the trimming image VT larger than the live image VL so that the stent image S that appears in the trimming image VT becomes larger than the stent image S that appears in the live image. The trimming image VT is a moving image clearer than the live image VL, and has a grade that can withstand enlarged displaying.

When an operator gives an instruction to stop imaging a live image VL to the device, the X-ray irradiation is stopped and imaging of the live image VL is stopped, thus terminating the generation of the trimming image VT. Thus, the operation of the X-ray equipment according to the present disclosure will be terminated.

As described above, according to the present disclosure, an X-ray equipment 1 may be provided in which in a moving image displaying an enlarged stent image S that appears in a live image VL, the visibility is improved by preventing the phenomenon of inverting the stent image S. For example, the present disclosure is equipped with the trimming unit 14 that performs editing that a specific one of two stent markers, which shows positions of an elongated stent image that appears in a superimposed frame Fg generated by superimposing source frames F which are sources of the live image VL, is made to be always oriented in the same direction. By editing a superimposed frame Fg continuously generated by the trimming unit 14, an object appears in the edited frame in the same orientation. Therefore, a phenomenon that an object to be display is inverted during the video playback as seen in the past may not occur.

The present disclosure may prevent an inversion of an object to be displayed, and therefore is suitable for blood vessel imaging. In the blood vessel imaging, a blood vessel appears in a superimposed frame Fg. When the display of the superimposed frame Fg is inverted like in a conventional configuration, the blood vessel that appears in the superimposed frame Fg is also inverted, the downstream side and the upstream side of the blood vessel that appears in the superimposed frame are inverted. In such a situation, it becomes undistinguishable which side of the superimposed frame Fg is the heart side, making it difficult to perform an operation. According to the present disclosure, since the display of the superimposed frame Fg is not inverted, the downstream side and the upstream side of the blood vessel that appears in the superimposed frame Fg is not inverted, which results in an easy operation.

According to the present disclosure, as described above, the orientation of the trimming frame Ftr in the upper and lower reference mode MV of the present disclosure may be set so that the upper end and the lower end of an object appear on the upper side and the lower side of the trimming frame Ftr, respectively. Further, the orientation of the trimming frame Ftr in the left and right reference mode MV of the present disclosure may be set so that the right end and the left end of an object appear on the right side and the left side of the trimming frame Ftr, respectively. In the same manner, the orientation of the trimming frame Ftr in the left and right reference mode MV of the present disclosure may be set so that the right end and the left end of an object appear on the upper side and the lower side of the trimming frame Ftr, respectively. Which orientation of the trimming frame Ftr should be determined depends on the layout on the screen when the trimming frame Ftr is displayed. An operator can select the orientation of the trimming frame Ftr which is the most visible trimming frame Ftr.

Further, as described, when the live image VL which is a moving image configured by the source frame F and the trimming image VT which is a moving image configured by the trimming frame Ftr are displayed side by side, an operator can carry out an operation while referring both images. Therefore, according to the aforementioned configuration, it becomes possible to provide an X-ray equipment 1 improved to make it easier for an operation to operate.

The present disclosure is not limited to the aforementioned configuration, and may be carried out by being modified as follows.

(1) In the aforementioned upper and lower reference mode MV, the orientation of the trimming frame Ftr is determined so that the upper end of an object appeared in the superimposed frame Fg is positioned on the upper end of the trimming frame Ftr and the lower end of the object (stent image S) appeared in the superimposed frame Fg is positioned on the lower end of the trimming frame Ftr. The upper and lower reference mode MV may be configured such that the orientation of the trimming frame Ftr is determined so that the upper end of an object appeared in the superimposed frame Fg is positioned on the right end of the trimming frame Ftr and the lower end of the object appeared in the superimposed frame Fg is positioned on the left end of the trimming frame Ftr.

Describing further, whether the upper side end and the lower side end of an object (stent image S) that appeared in the superimposed frame Fg in the upper and lower reference mode MV is positioned which of the upper side, the lower side, the left side, and the right side of the trimming frame Ftr may be changed arbitrarily in accordance with the display manner of the trimming image VT. At this time, when one end of the stent image S is determined to be positioned on the upper side or the lower side, the other end is positioned on the lower side or the upper side. Further, when one end of the stent image S is determined to be positioned on the right side or the left side, the other end is positioned on the left side or the right side.

(2) In the same manner, whether the right side end and the left side end of an object that appeared in the superimposed frame Fg in the left and right reference mode MV and the stent marker specification mode is positioned on which of the upper side, the lower side, the left side, and the right side of the trimming frame Ftr may be changed arbitrarily in accordance with the display manner of the trimming image VT. For example, when one end of the stent image S is determined to be positioned on the upper side or the lower side, the other end is positioned on the lower side or the upper side. Further, when one end of the stent image S is determined to be positioned on the right side or the left side, the other end is positioned on the left side or the right side.

(3) The aforementioned Example is directed to a medical device, but the present disclosure may be applied to an industrial and/or nuclear device.

(4) The X-ray in the aforementioned Example is one example of the radiation in the present disclosure. Therefore, the present disclosure can also be applied to a radiation other than an X-ray.

(5) In the aforementioned Example, the explanation was made considering the treatment of angoiostenosis, but the present disclosure may be applied to insertion surgery of artificial heart valve. Further, the present disclosure can also be used for the purpose of confirming the status of a device inserted in a body.

(6) In the aforementioned Example, it is configured such that a superimposed frame is generated by superimposing 4 (four) source frames, but the present disclosure allows to increase and decrease the number of source frames required to generate a superimposed frame. For the number of source frames required to generate a superimposed frame may be 8 (eight).

<Other Modes>

In the aforementioned configuration, an upper and lower reference mode MV, a left and right reference mode MH, and a stent marker specification mode are explained. However, the present disclosure may be configured to provide another mode different from the above modes to be operated. Hereinafter, two modes, a reference point reference mode MP and a region reference mode MR, will be explained.

<Reference Point Reference Mode MP>

Figure 15:
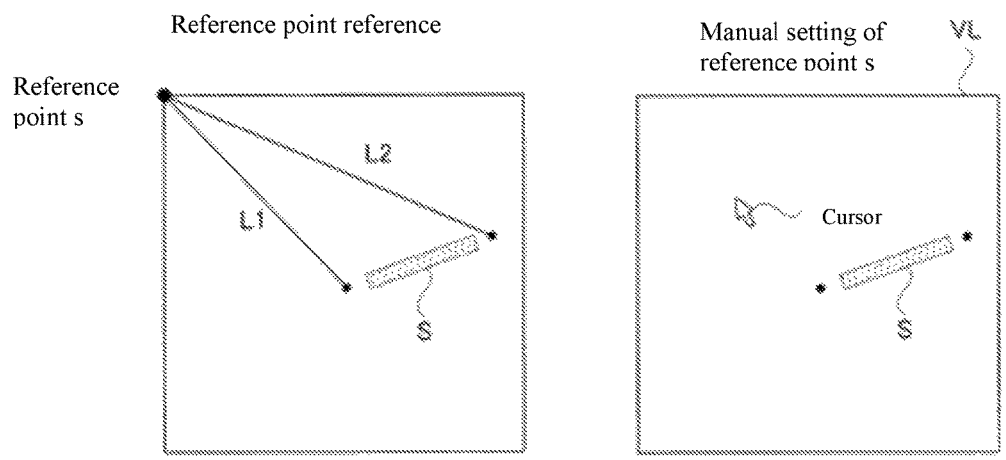
FIG. 15 is a pattern diagram that explains a configuration of a first modified Example of the present disclosure.

The left side of FIG. 15 explains a reference point reference mode MP of the present disclosure. In the reference point reference mode MP, a reference point s is set in a superimposed frame Fg, and a display orientation of a trimming frame Ftr is determined with reference to the reference point s. The reference point s on the left side of FIG. 15 is positioned at the left upper end portion of the superimposed frame Fg, and does not change among superimposed frames Fg1, Fg2, . . . generated consecutively.

The right side of FIG. 15 shows a state in which an operator sets a reference point s. During imaging a live image, a live image VL is displayed on a display unit 25. An operator can move a cursor on the display unit 25 using an attached mouse (not shown). An operator can move the cursor to a point where a reference point s of a live image VL is to be set. When an operator clicks a mouse button, a reference point s is set on a superimposed frame Fg. For example, the trimming unit 14 recognizes the position on the superimposed frame Fg corresponding to the position on the live image VL specified by an operator as a reference point s and operates.

The reference point s is not always required to be manually set by an operator. As shown in FIG. 16, the position of the reference point s may be set in advance. A storage unit 28 of the X-ray equipment 1 includes a table T associated with preset data every imaging purpose. This preset data includes data on controls of X-ray tube 3, such as, e.g., a tube voltage, a tube current, a pulse width, a pulse interval. When an operator specifies the imaging purpose via the console 26, the X-ray tube control unit 6 reads out the control conditions of the X-ray tube 3 corresponding to the specified imaging purpose from the storage unit 28 and operates. By providing an term relating to a position of a reference point s in this table T and associating the imaging purpose with the position of the reference point s, mere specifying the imaging purpose by the operator causes an automatic determination of the position of the reference point s on the superimposed frame Fg. For example, when the operator specifies right coronary artery imaging for the imaging purpose via the console 26, the trimming unit 14 reads out the position of the reference point s corresponding to the specified imaging purpose from the storage unit 28, recognizes that the reference point s is positioned at the right upper end, and operates.

The trimming unit 14 recognizes the position of the stent markers positioned on both ends of the stent image S that appears in the superimposed frame Fg as shown on the left side of FIG. 15, and calculates the distance L1 from the reference point s to one of the stent markers and the distance L2 from the reference point s from the other stent marker. Then, as shown in FIG. 17, the orientation of the trimming frame is determined so that one of both ends of the stent image which is closer to the reference point s is positioned on the upper side of the trimming frame Ftr and the other is positioned on the lower side of the trimming frame Ftr. In FIG. 17, the distance L1 from the end A of the stent image S to the reference point s is shorter than the distance L2 from the end B of the stent image S to the reference point s, and therefore the trimming frame Ftr is displayed on the display unit 25 so that the end A of the stent image S is positioned on the upper side and the end B is positioned on the lower side. As described above, this reference point reference mode MH is a mode that determines the direction of the trimming frame Ftr by determining that of both ends of the stent image S that appears in a superimposed image, the end closer to and the end farther to the reference point s set on the superimposed frame Fg appears which of the upper, lower, left, and right side of the trimming frame Ftr.

Figure 18:
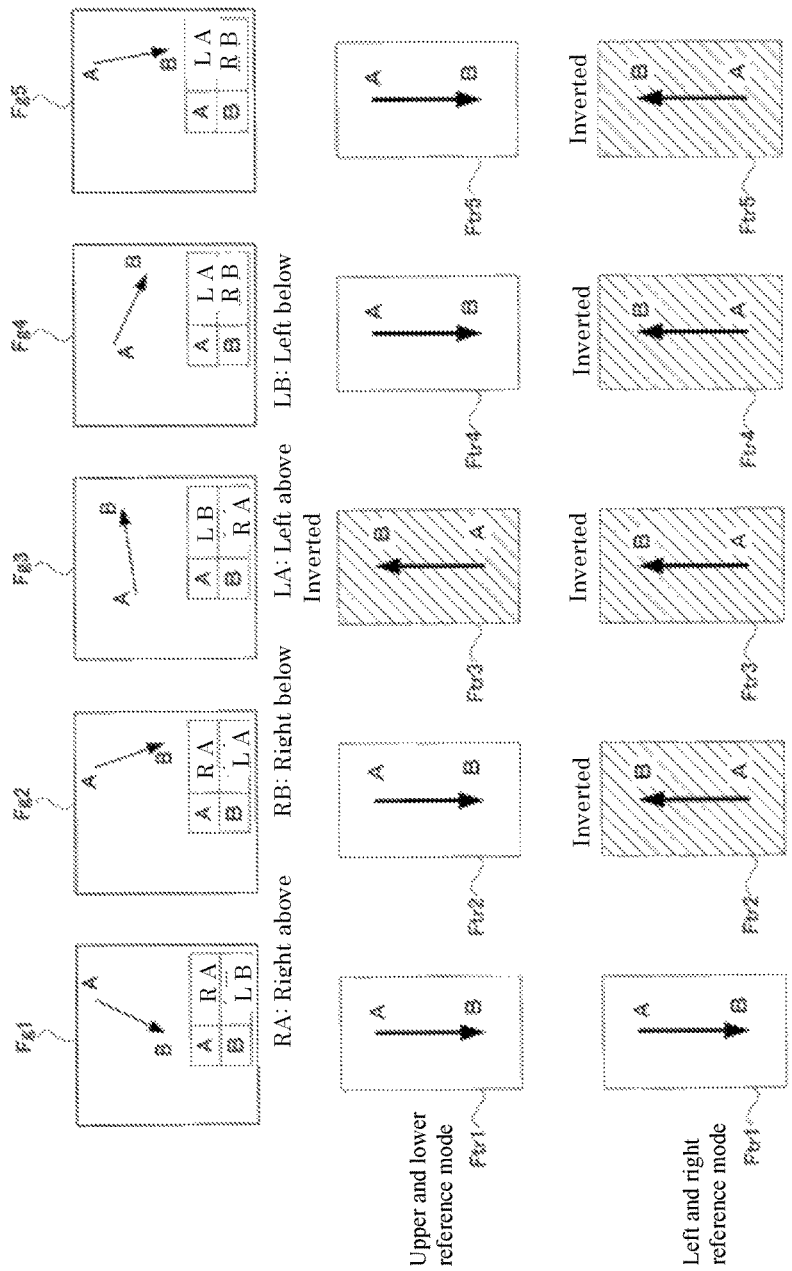
FIG. 18 is a pattern diagram that explains a configuration of a first modified Example of the present disclosure.
Figure 19:
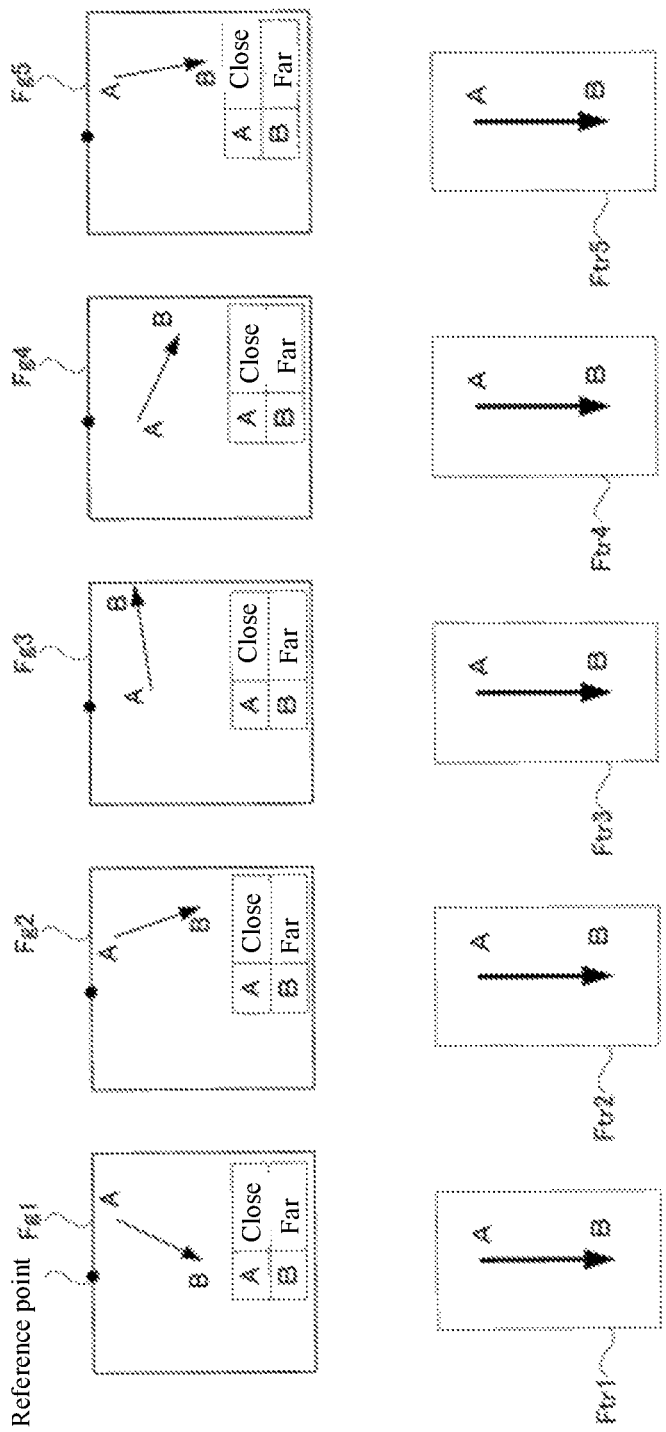
FIG. 19 is a pattern diagram that explains a configuration of a first modified Example of the present disclosure.

FIG. 18 and FIG. 19 illustrate behaviors of the stent image S in which the reference point reference mode MP is advantageous. As shown in the upper portion of FIG. 12, in cases where a stent image S is appeared in a swinging manner in each of superimposed frames Fg1 to Fg5, it is advantageous to generate trimming frames Ftr1 to Ftr5 in accordance with the reference point reference mode MP. In cases where a stent image S rotates vigorously among superimposed frames Fg1 to Fg5, as shown in FIG. 18, by the upper and lower reference mode MV and the left and right reference mode MH, there are cases that the inversion of the trimming frame Ftr may not be prevented sufficiently. Further, even in the stent marker specification mode, it is hard to accurately trace the ends of the rotating stent image S.

Especially, in cases where a stent is being inserted in a coronary artery, looking the generated superimposed frames Fg in order, it may be seen that the stent image S that appears in the frame has certain motions. This is derived from the fact that the coronary artery repeats a certain movement in accordance with the heart beat. Both ends of the stent image S in the superimposed frame Fg repeat a certain fixed behavior pattern. Further, due to how the coronary artery stretches and how the heart moves, the stent image S in the superimposed frame Fg tends to move such that one end of the stent image rotates with respect to the other end. As described above, in this manner, the behavior patterns of both ends of the stent image S seen among superimposed frames Fg are considerably limited. Therefore, even if the stent image S rotates within each superimposed frame Fg, one end of the stent image S may always be positioned near a position in the superimposed frame Fg, and the other end of the stent image S may not always approach the position. Therefore, as shown in FIG. 19, when the orientation of the trimming frame Ftr is determined by adopting the reference point reference mode MP, the inversion of the trimming frame Ftr may be suppressed.

<Region Reference Mode MR>

Figure 20:
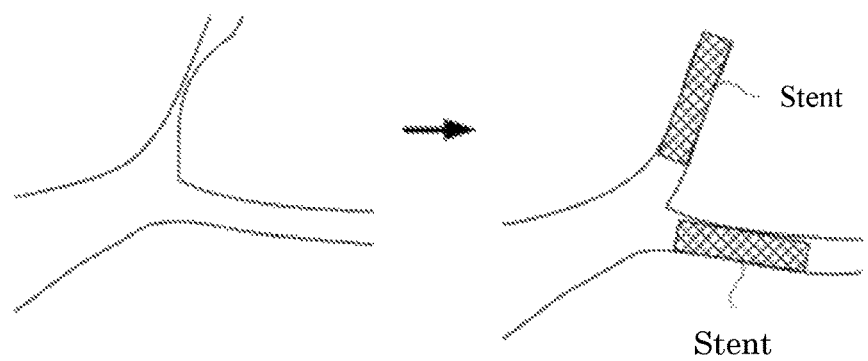
FIG. 20 is a pattern diagram that explains a configuration of a first modified Example of the present disclosure.

Finally, a region reference mode MR will be explained. The region reference mode MR is particularly effective when multiple stent images S appear in superimposed frames Fg. FIG. 20 shows a state in which coronary artery surgery is being performed. As shown on the left side of FIG. 20, when one of arteries branched into two is constricted, a measurement is taken to arrange stents for both of branches (see the right side of FIG. 20). This is because if the stent is placed only in the narrowed blood vessel, the blood flow of the narrowed branch may be deteriorated.

Figure 21:
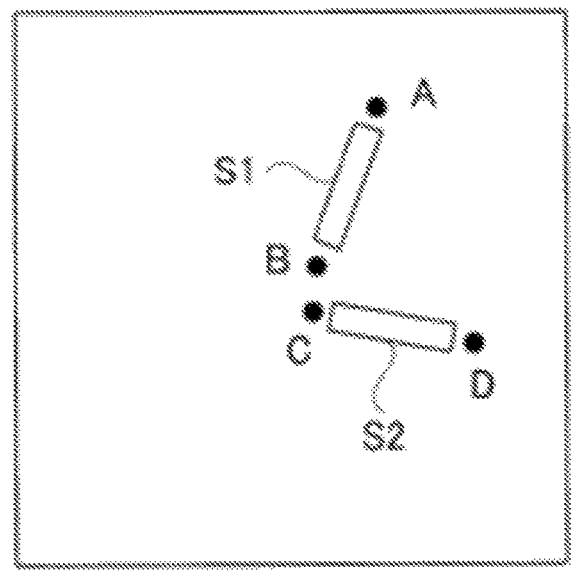
FIG. 21 is a pattern diagram that explains a configuration of a first modified Example of the present disclosure.

In the case of such surgery, as shown in FIG. 21, two stent images S1 and S2 appear in the superimposed frame Fg at the same time. It is assumed that a trimming frame Ftr that extracted a stent image S1 is necessary. When a plurality of stent images appear in the superimposed frame Fg which becomes a base of the trimming frame Ftr, the inversion of the stent image on the trimming frame Ftr is likely to occur. FIG. 22 and FIG. 23 explain the situation. FIG. 22 shows a case where only the stent image S1 appears in the superimposed frame Fg. In cases where a trimming frame Ftr is generated from this superimposed frame Fg, supposing that the left and right reference mode MH is selected, the orientation of the trimming frame Ftr is determined so that the end A of the stent image S1 positioned on the right side of the frame is positioned on the upper side of the trimming frame Ftr and the ed B of the stent image S1 positioned on the left side of the frame is positioned on the lower side of the trimming frame Ftr.

However, as shown in FIG. 23, if the stent images S1 and S2 appear in the superimposed frame Fg, it is required that the orientation of the trimming frame Ftr is determined so that the end A of the stent image S1 positioned on the right side of the frame is positioned on the upper side of the trimming frame Ftr and the end B of the stent image S1 positioned on the left side of the frame is positioned on the lower side of the trimming frame Ftr. However, there is a possibility that the orientation of the trimming frame Ftr is determined so that the end A is positioned on the lower side of the trimming frame Ftr because the end A of the stent image S1 is on the left side of the end D of the stent image S2. On the other hand, when the end D of the stent image S2 frames out from the superimposed frame Fg, the orientation of the trimming frame Ftr is determined so that the end A of the stent image S1 is positioned on the right side of the trimming frame Frt because the end A of the stent image S1 is on the right side of the stent image S1 than the end B. In this way, a plurality of stent images that appear in the superimposed frame Fg cause inversion of the trimming frame Ftr.

Figure 24:
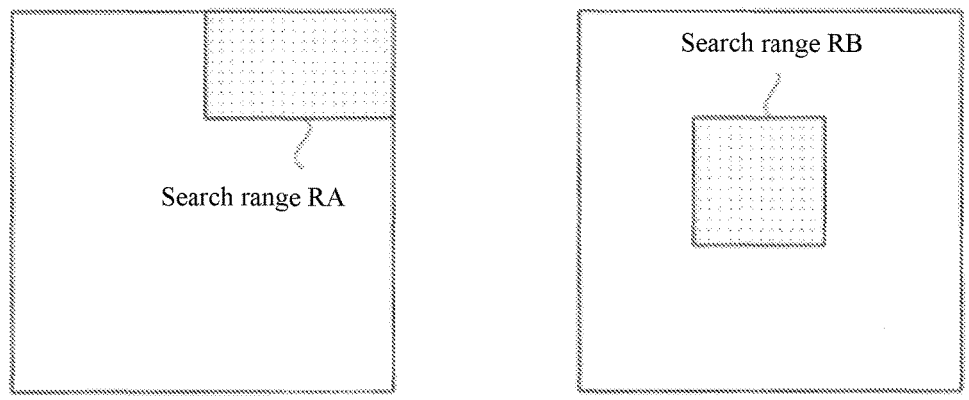
FIG. 24 is a pattern diagram that explains a configuration of a first modified Example of the present disclosure.

The region reference mode MR is devised so that the trimming frame Ftr is not inverted even in cases where a plurality of stent images appear in a superimposed frame Fg as shown in FIG. 21. In the storage unit 28, data defining a search range RA and a search range RB, which are ranges on the superimposed frame Fg, are stored. When the region reference mode MR is selected, the trimming unit 14 reads out these data from the storage unit 28 and recognizes the search range RA and the search range RB on the superimposed frame Fg shown in FIG. 24 to operate.

The trimming unit 14 determines the orientation of the trimming frame Ftr so that the end A of the stent image S1 positioned in the search range RA set on the superimposed frame Fg comes on the upper side of the trimming frame Ftr and the end B of the stent image S1 positioned within the search range RB comes to the lower side of the trimming frame Ftr.

The search range RA indicates the movable range of the end A of the stent image S1 on the superimposed frame Fg and indicates the movable range of the end B of the stent image S1 on the superimposed frame Fg. In cases where a stent is being inserted in the coronary artery, looking the generated superimposed frame Fg in order, the stent image S that appears in the frame has certain fixed movements. This is derived from the fact that the coronary artery repeats a certain movement in accordance with the heartbeat. Both ends of the stent image S in the superimposed frame Fg repeat a certain fixed behavior pattern. As described above, in this manner, the behavior patterns of both ends of the stent image S seen among superimposed frames Fg are considerably limited. Therefore, the movable range of the end A of the stent image S1 in the superimposed frame Fg and the movable range of the end B are determined.

Figure 25:
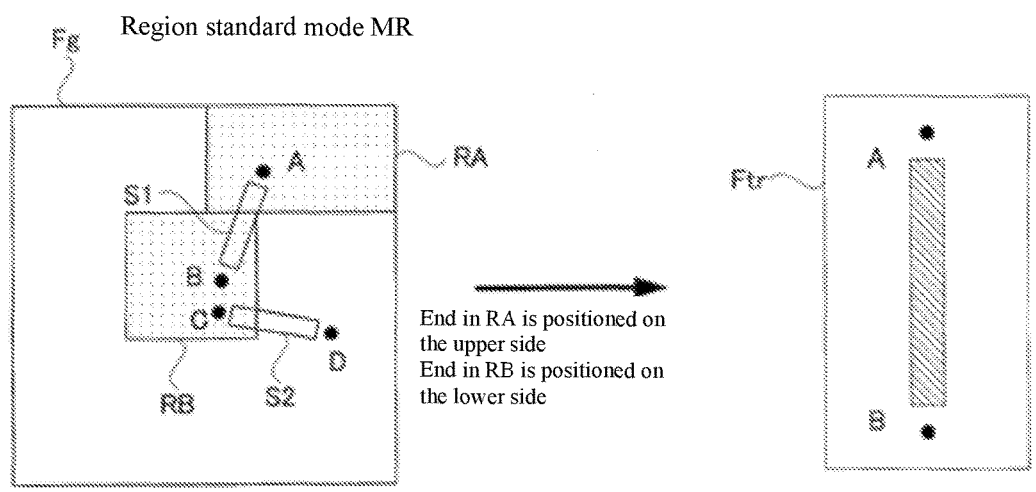
FIG. 25 is a pattern diagram that explains a configuration of a first modified Example of the present disclosure.
Figure 26:
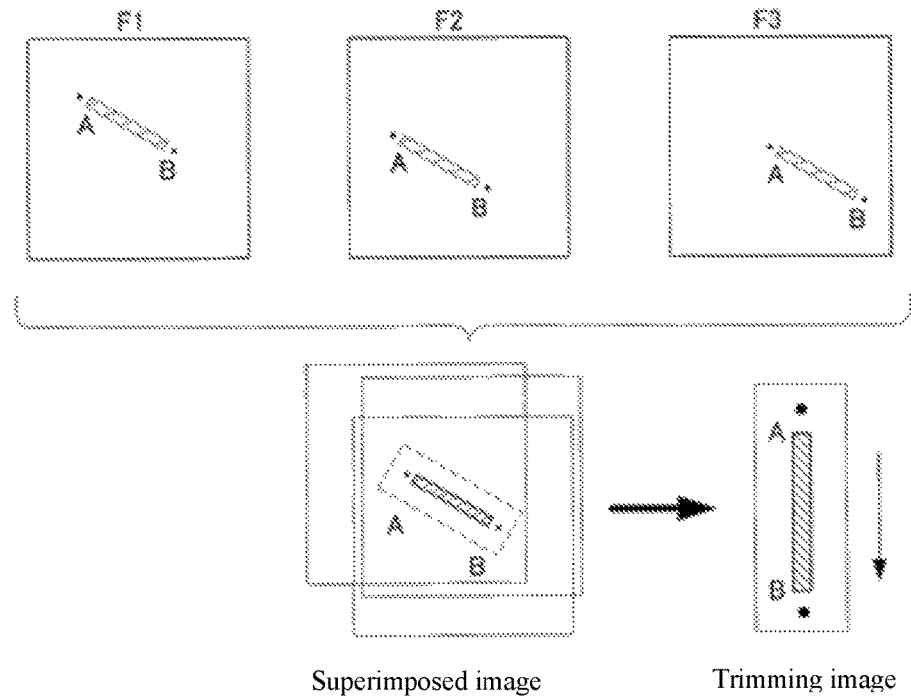
FIG. 26 is a pattern diagram that explains a radiographic imaging device of a conventional configuration.
Figure 27:
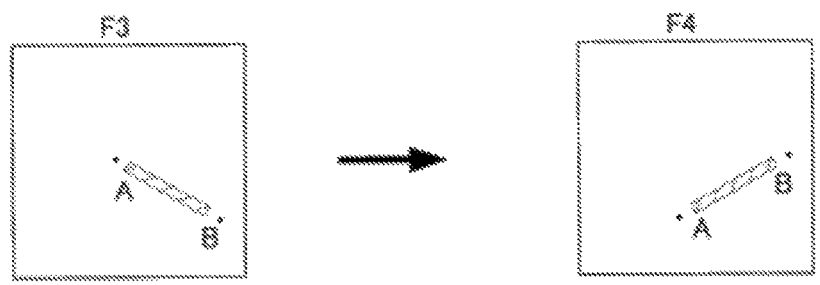
FIG. 27 is a pattern diagram that explains problems of a radiographic imaging device of a conventional configuration.
Figure 28:
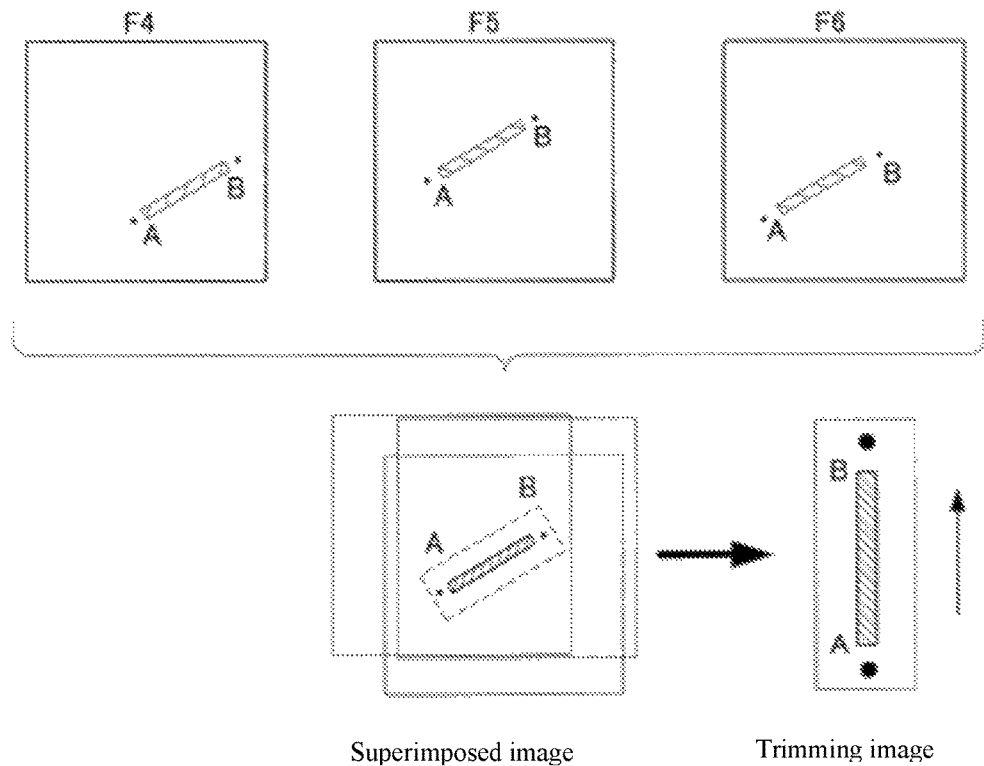
FIG. 28 is a pattern diagram that explains problems of a radiographic imaging device of a conventional configuration.
Figure 29:
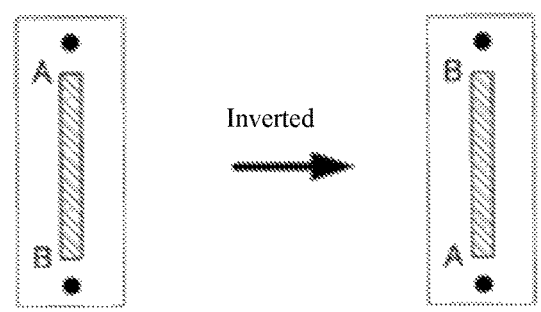
FIG. 29 is a pattern diagram that explains problems of a radiographic imaging device of a conventional configuration.
Figure 30:
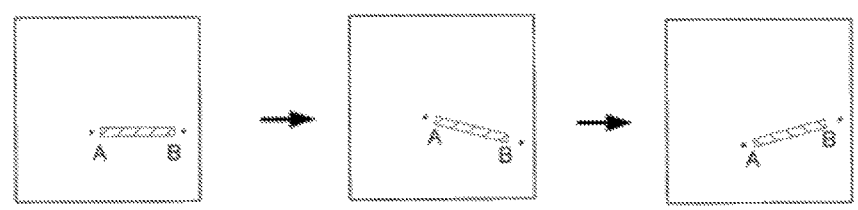
FIG. 30 is a pattern diagram that explains problems of a radiographic imaging device of a conventional configuration.

Although the search range RA and the search range RB do not overlap in FIG. 25, it is also possible to set so that the search range RA partially overlaps the search range RB. Further, the search range RA and the search range RB may be set within the same range. Further, in this modified Example, it may be configured such that only one of the search range RA and the search range RB is set.

According to the method of determining the orientation of the trimming frame Ftr shown in FIG. 25, the end D of the stent image S2, which is the cause of the inversion of the trimming frame Ftr in FIG. 23, is not taken into account in determining the orientation of the trimming frame Ftr. Therefore, according to the region reference mode MR, even if a plurality of stent images appear in the superimposed frame Fg, it is possible to suppress the inversion of the trimming frame Ftr.

DESCRIPTION OF THE SYMBOLS

F frame
Fg superimposed frame
3 X-ray tube (radiation source)
4 FPD (detection means)
11 frame generation unit (frame generation means)
12 alignment processing unit (alignment processing means)
13 superimposed frame generation unit (superimposed frame generation means)
14 trimming unit (editing means)
25 display unit (display means)
26 console (input means)

INDUSTRIAL APPLICABILITY

As described above, the present disclosure is suitable for a medical field.

The invention claimed is:
1. A radiographic imaging device comprising:
   a radiation source that irradiates radiation toward a subject;
   a detector that detects the radiation passed through the subject;
   a display configured to display images;
   a console configured to receive a selection of a mode;
   a processor configured to receive information of the selected mode;
   wherein the processor is further configured to:
      generate a plurality of source frames based on a detection signal output by the detector;
      recognize a plurality of feature points indicating a position of an object that appears in each of the plurality of source frames;
      align the plurality of source frames so that corresponding feature points overlap with each other;
      repeatedly generate a superimposed frame in which images of the object overlap with each other by superimposing the aligned plurality of source frames;
   modify superimposed frames repeatedly so that a particular feature point of the feature points that appear in the repeatedly generated superimposed frame orients in a same direction on a modified frame when the selected mode is upper and lower reference mode, the particular feature point being located relatively topmost or bottommost in the feature points, or
   modify the superimposed frames repeatedly so that the particular feature point of the feature points that appear in the repeatedly generated superimposed frame orients in a same direction on a modified frame when the selected mode is left and right reference mode, the particular feature point being located relatively leftmost or rightmost in the feature points; and
   control the display so as to repeatedly display the modified frame.
2. The radiographic imaging device as recited in claim 1, wherein the particular feature point appearing in the super- imposed frame becomes a reference of the modifying based on a positional relationship of the particular feature point or an instruction of an operator.

3. The radiographic imaging device as recited in claim 1, wherein the processor is configured to repeatedly generate a modified frame in which the object that appears in each superimposed frame is enlarged by subjecting trimming processing to each of the superimposed frames so as to provide a rectangular region including the object.

4. The radiographic imaging device as recited in claim 1, wherein the console is further configured to allow an operator's input of selecting an upper and lower reference mode that determines an orientation by determining that an upper end and a lower end of the object that appears in the superimposed frame appear in any one of an upper side, a lower side, a left side, or a right side of the frame.

5. The radiographic imaging device as recited in claim 4,
wherein the processor is configured to repeatedly generate a modified frame in which the object that appears in each superimposed frame is enlarged by subjecting trimming processing to each of the superimposed frames so as to provide a rectangular region including the object, and
wherein when the upper and the lower reference mode is selected, the processor determines the orientation so that the upper end of the object appeared in the superimposed frame is positioned on an upper end of the modified frame and the lower end of the object appeared in the superimposed frame is positioned on a lower end of the modified frame.

6. The radiographic imaging device as recited in claim 1, wherein the console is further configured to allow an operator's input of selecting a left and right reference mode that determines an orientation by determining that a right end and a left end of the object that appears in the superimposed frame appear in any one of an upper side, a lower side, a left side, or a right side of the frame.

7. The radiographic imaging device as recited in claim 6,
wherein the processor is further configured to repeatedly generate a modified frame in which the object that appears in each superimposed frame is enlarged by subjecting trimming processing to each of the superimposed frames so as to provide a rectangular region including the object, and
wherein when the left and right reference mode is selected, the processor determines the orientation so that the right end of the object that appears in the superimposed frame is positioned on an upper end of the modified frame and the left end of the object that appears in the superimposed frame is positioned on a lower end of the modified frame.

8. The radiographic imaging device as recited in claim 6, wherein the processor is further configured to repeatedly generate a modified frame in which the object that appears in each superimposed frame is enlarged by subjecting trimming processing to each of the superimposed frames so as to provide a rectangular region including the object, and
wherein when the left and right reference mode is selected, the processor determines the orientation so that the right end of the object that appears in the superimposed frame is positioned on a right end of the modified frame and the left end of the object that appears in the superimposed frame is positioned on a left end of the modified frame.

9. The radiographic imaging device as recited in claim 1, wherein the console is further configured to allow an operator's input of selecting a feature point specification mode that determines an orientation by determining that one of a plurality of features specified by an operator that appears in the superimposed frame appear in any one of an upper side, a lower side, a left side, or a right side of the frame.

10. The radiographic imaging device as recited in claim 1, wherein the console is further configured to allow an operator's input of selecting a reference point reference mode that determines an orientation by determining that a feature point closer to a reference point and a feature point farther to the reference point among a plurality of feature points that appears in the superimposed frame appears in any one of an upper side, a lower side, a left side, or a right side of the frame.

11. The radiographic imaging device as recited in claim 1, wherein the console is further configured to allow an operator's input of selecting a reference point reference mode that determines an orientation by determining that a feature point belonging to a region specified on the superimposed frame among a plurality of feature points that appears in the superimposed frame appears in any one of an upper side, a lower side, a left side, or a right side of the frame.

12. The radiographic imaging device as recited in claim 1, wherein the object is a stent.

13. The radiographic imaging device as recited in claim 1, wherein the display is further configured to display a live image which is a moving image configured by the plurality of source frames and another moving image configured by the modified frame side by side.

14. A radiographic imaging method comprising:
irradiating radiation toward a subject;
detecting the radiation passed through the subject;
generating a plurality of source frames based on a detection signal generated by the detecting step;
recognizing a plurality of feature points indicating a position of an object that appears in each of the plurality of source frames;
aligning the plurality of source frames so that corresponding feature points overlap with each other;
repeatedly generating a superimposed frame in which images of the object overlap with each other by superimposing the aligned plurality of source frames;
modify superimposed frames repeatedly so that a particular feature point of the feature points that appear in the repeatedly generated superimposed frame orients in a same direction on a modified frame when a selected mode is upper and lower reference mode, the particular feature point being located relatively topmost or bottommost in the feature points, or
modify the superimposed frames repeatedly so that the particular feature point of the feature points that appear in the repeatedly generated superimposed frame orients in a same direction on a modified frame when the selected mode is left and right reference mode, the particular feature point being located relatively leftmost or rightmost in the feature points; and
repeatedly displaying the modified frame.

15. The radiographic imaging method as recited in claim 14, further comprising:
determining one of features appearing in the superimposed frame that becomes a reference of the modifying based on a positional relationship of the particular feature point or an instruction of an operator.

16. The radiographic imaging method as recited in claim 14, further comprising:
repeatedly generating the modified frame in which the object that appears in each superimposed frame is enlarged by subjecting editing processing to each of the superimposed frames so as to provide a rectangular region including the object.

17. The radiographic imaging method as recited in claim 14, further comprising:
selecting an upper and lower reference mode that determines an orientation of the modifying by determining that an upper end and a lower end of the object that appears in the superimposed frame appear in any one of an upper side, a lower side, a left side, or a right side of the frame.

18. A radiographic imaging device comprising:
a radiation source that irradiates radiation toward a subject;
a detector that detects the radiation passed through the subject;
a display configured to display a plurality of source frames generated based on a detection signal output by the detector; and
a processor configured to:
receive the detection signal output by the detector;
generate the plurality of source frames based on the detection signal output by the detector;
recognize a plurality of feature points indicating a position of an object that appears in each of the plurality of source frames;
align the plurality of source frames so that corresponding feature points overlap with each other;
repeatedly generate a superimposed frame in which images of the object overlap with each other by superimposing the aligned plurality of source frames;
modify superimposed frames repeatedly so that a particular feature point of the feature points that appear in the repeatedly generated superimposed frame orients in a same direction on a modified frame when a selected mode is upper and lower reference mode, the particular feature point being located relatively topmost or bottommost in the feature points, or
modify the superimposed frames repeatedly so that the particular feature point of the feature points that appear in the repeatedly generated superimposed frame orients in a same direction on a modified frame when the selected mode is left and right reference mode, the particular feature point being located relatively leftmost or rightmost in the feature points; and
control the display so as to repeatedly display the modified frame.

19. The radiographic imaging device as recited in claim 18, wherein the processor is a central processing unit (CPU).

20. A radiographic imaging device comprising:
a radiation source that irradiates radiation toward a subject;
detector that detects the radiation passed through the subject;
a display configured to display a superimposed frame generated to superimpose source frames which are based on a detection signal output by the detector;
a console configured to receive selection of a feature point from a plurality of feature points in the superimposed frame;
a processor that receives information of the selected feature point;
wherein the processor is further configured to:
generate a plurality of source frames based on a detection signal output by the detector;
recognize a plurality of feature points indicating a position of an object that appears in each of the plurality of source frames;
align the plurality of source frames so that corresponding feature points overlap with each other;
repeatedly generate a superimposed frame in which images of the object overlap with each other by superimposing the aligned plurality of source frames;
modify superimposed frames repeatedly so that a particular feature point that appears in the repeatedly generated superimposed frame orients in a same direction on a modified frame, the particular feature point being selected through the console; and
control the display so as to repeatedly display the modified frame.

21. A radiographic imaging device comprising:
a radiation source that irradiates radiation toward a subject;
a detector that detects the radiation passed through the subject;
a display configured to display an image;
a console configured to receive an operation of a decision for reference position in the image;
a processor configured to receive the decision for the reference position;
wherein the processor is further configured to:
generate a plurality of source frames based on a detection signal output by the detector;
recognize a plurality of feature points indicating a position of an object that appears in each of the plurality of source frames;
align the plurality of source frames so that corresponding feature points overlap with each other;
repeatedly generate a superimposed frame in which images of the object overlap with each other by superimposing the aligned plurality of source frames;
modify superimposed frames repeatedly so that a particular feature point of the feature points that appear in the repeatedly generated superimposed frame orients in a same direction on a modified frame, the particular feature point being located relatively farthest or nearest to a reference position in the feature points; and
control the display so as to repeatedly display the modified frame.

22. A radiographic imaging device comprising:
a radiation source that irradiates radiation toward a subject;
a detector that detects the radiation passed through the subject;
a display configured to display an image;
a memory that stores information of a range of the image;
a processor configured to receive the information of the range;
wherein the processor is further configured to:
generate a plurality of source frames based on a detection signal output by the detector;
recognize a plurality of feature points indicating a position of an object that appears in each of the plurality of source frames;
align the plurality of source frames so that corresponding feature points overlap with each other;

repeatedly generate a superimposed frame in which images of the object overlap with each other by superimposing the aligned plurality of source frames;

modify superimposed frames repeatedly so that a particular feature point of the feature points that appear in the repeatedly generated superimposed frame orients in a same direction on a modified frame, the particular feature point existing in the range; and control the display so as to repeatedly display the modified frame.

* * * * *